US005830735A

United States Patent [19]
Andreoli et al.

[11] Patent Number: 5,830,735
[45] Date of Patent: Nov. 3, 1998

[54] METHOD FOR PRODUCING LIPOLYTIC ENZYMES USING TRANSFORMED PSEUDOMONAS

[75] Inventors: Peter Michael Andreoli, Bellegem-Kortrijk, Belgium; Maria Mathilde Josphina Cox, Delft; Farrokh Farin, Hazerswoude-Rijndijk, both of Netherlands; Suzanne Wohlfarth-Rippel, Dortmund, Germany

[73] Assignee: Gist-Brocades NV, Delft, Netherlands

[21] Appl. No.: 983,822

[22] Filed: Dec. 1, 1992

Related U.S. Application Data

[60] Division of Ser. No. 415,142, Sep. 25, 1989, Pat. No. 5,278,066, which is a continuation-in-part of Ser. No. 154,182, Feb. 9, 1988, abandoned, which is a continuation-in-part of Ser. No. 34,418, Mar. 6, 1987, Pat. No. 4,933,287.

[51] Int. Cl.$^6$ .............................. C12N 9/20; C12N 15/78; C12P 21/00
[52] U.S. Cl. ..................... 435/198; 435/69.1; 435/253.3; 435/874
[58] Field of Search ................................... 435/69.1, 198

[56] References Cited

U.S. PATENT DOCUMENTS

| | | | |
|---|---|---|---|
| 3,950,277 | 4/1976 | Stewart et al. | 252/541 |
| 4,663,280 | 5/1987 | Sloma | 435/68 |
| 4,933,287 | 6/1990 | Farin et al. | 435/198 |
| 5,030,240 | 7/1991 | Wiersema et al. | 8/111 |
| 5,153,135 | 10/1992 | Farin et al. | 435/253.3 |
| 5,278,066 | 1/1994 | Andreoli et al. | 435/252.34 |

FOREIGN PATENT DOCUMENTS

| | | |
|---|---|---|
| 835343 | 2/1970 | Canada . |
| 0 130 064 | 1/1985 | European Pat. Off. . |
| 0 206 390 | 12/1986 | European Pat. Off. . |
| 0 206 396 | 12/1986 | European Pat. Off. . |
| 0 218 272 | 4/1987 | European Pat. Off. . |
| 0 224 294 | 6/1987 | European Pat. Off. . |
| 0 243 338 | 10/1987 | European Pat. Off. . |
| 0 253 455 | 1/1988 | European Pat. Off. . |
| 0 275 598 | 7/1988 | European Pat. Off. . |
| 0 305 216 | 3/1989 | European Pat. Off. . |
| 0 331 376 | 9/1989 | European Pat. Off. . |
| 0334 462 | 9/1989 | European Pat. Off. . |
| 1293613 | 5/1970 | United Kingdom . |
| 1373034 | 2/1971 | United Kingdom . |
| 1442418 | 12/1973 | United Kingdom . |

OTHER PUBLICATIONS

Wohlfarth, S., et al., Journal of General Microbiology, vol. 134, pp. 433–440, Feb., 1988.
Kugimiya, W., et al., Biochemical and Biophysical Research Communications, vol. 141, pp. 185–190, Nov., 1986.
Wohlfarth, S., et al., Journal of General Microbiology, vol. 138, pp. 1325–1335, 1992.
Andree et al., "Lipases as Detergent Components", *J. Appl. Biochem.*, vol. 2, pp. 218–229 (1980).
Bagdasarian et al., "Specific–purpose Plasmid Cloning Vectors . . . ", *Gene*, vol. 16, pp. 237–247 (1981).
Bodmer et al., "Molecular Cloning of a Human Gastric Lipase and Expression of the Enzyme in Yeast", *Biochem. Biophys. Acta*, vol. 909, pp. 237–244 (1987).
Davison et al., "Vectors with Restriction Site Banks . . . ", *Gene*, vol. 51, pp. 275–280 (1987).
Deininger, "Random Subcloning of Sonicated DNA: Application to Shotgun DNA Sequence Analysis", *Anal. Biochem.*, vol. 129, pp. 216–223 (1983).
Donovan and Kushner, "Cloning and Physical Analysis of the pyrF Gene (Coding for Orotidine–5'–phosphate Decarboxylase (from *Escherichia coli* K–12", *Gene*, vol. 25, pp. 39–48 (1983).
Dagert and Ehrlich, "Prolonged Incubation in Calcium Chloride Improves the Competence of *Escherichia coli* Cells", *Gene*, vol. 6, pp. 23–28 (1979).
Feinberg and Vogelstein, "A Technique for Radiolabeling DNA Restriction Endonuclease Fragments to High Specific Activity", *Anal. Biochem.*, vol. 132, pp. 6–13 (1983).
Friedman et al., "Construction of a Broad Host Range Cosmid Cloning Vector and its Use in the Genetic Analysis of Rhizobium Mutants", *Gene*, vol. 18, pp. 289–296 (1982).
Gryczan and Dubnau, "Direct Selection of Recombinant Plamsids in *Bacillus Subtilis*", *Gene*, vol. 20, pp. 459–469 (1982).
Haferburg and Kleber, "Extrazellulare Lipase aus Acinetobacter Calcoaceticus", *Acta Biotechnologica*, vol. 2, pp. 337–342 (1982).
Hanahan, "Studies on Transformation of *Escherichia coli* With Plasmids", *J. Mol. Biol.*, vol. 166, pp. 557–580 (1983).
Harris, "Expression of Eukaryotic Genes in *E. coli*", *Genetic Engineering*, vol. 4, pp. 127–185 (1983).
von Heijne, "Net N—C Charge Imbalance may be Important for Signal Sequence Function in Bacteria", *Gene*, vol. 192, pp. 287–290 (1986).
Himeno et al., "Protein Secretion in *Bacillus subtilis* as Influenced by the Combination of Signal Sequence and the Following Mature Portion", *FEMS Microbiol. Letters*, vol. 35, pp. 17–21 (1986).
Kouker and Jaeger, "Specific and Sensitive Plate Assay for Bacterial Lipases", *Appl. Env. Microbiol.*, vol. 53, pp. 211–213 (1987).
Kugimiya et al., "Molecular Cloning and Nucleotide Sequence of the Lipase Gene from *Pseudomonas Fragi*", *Biochem. Biophys. Res. Comm.*, vol. 141, pp. 185–190 (1986).
Laemmli, "Cleavage of Structural Proteins during the Assembly of the Head of Bacteriophage T4", *Nature*, vol. 227, pp. 680–685 (1970).
Laskin and Lechevalier (Eds.), *Handbook of Microbiology*, vol. II (1973).

(List continued on next page.)

*Primary Examiner*—Robert A. Wax
*Assistant Examiner*—Eric Grimes
*Attorney, Agent, or Firm*—Barbara Rae-Venter

[57] ABSTRACT

Novel microbial host strains are provided which are transformed by a vector molecule comprising a DNA fragment encoding a lipolytic enzyme and a marker for selection, capable of producing active lipase. Said DNA fragment is preferably derived from a Pseudomonas species.

7 Claims, 24 Drawing Sheets

OTHER PUBLICATIONS

Maase and van Tilburg, "The Benefit of Detergent Enzymes under Changing Washing Conditions", *J. Amer. Oil Chem. Soc.*, vol. 60, pp. 1672–1675 (1983).

Odera et al., "Molecular of Lipase Genes from *Alcaligenes denitrificans* and Their Expression in *Escherichia coli*", *J. Ferment. Technol.*, vol. 64, pp. 363–371 (1986).

Olsen et al., "Development of Broad–Host–Range Vectors and Gene Banks: Self–cloning of the *Pseudomonas aeruginosa* PAO", *J. Bacteriol.*, vol. 150, pp. 60–69 (1982).

Sarvas, "Protein Secretion in Bacilli", *Current Topics in Microbiology and Immunol.*, vol. 125, pp. 103–125 (1986).

Staskawicz et al. "Molecular Charcterization of Cloned Avirulence Genes from Race 0 and Race 1 of *Pseudomonas syringae* pv. *glycinea*", *J. Bacteriol.*, vol. 169. pp. 5789–5794 (1987).

Stuer et al., "Purification of Extracellular Lipase from *Pesudomonas aeruginosa*", *J. Bacteriol.*, vol. 168, pp. 1070–1074 (1986).

Tsuchido et al., "Destruction of the Outer Membrane Permeability Barrier of *Escherichia coli* by Heat Treatment", *Appl. Environmental Microbiol.*, vol. 50, pp. 298–303 (1985).

Vasil et al., "Cloning of a Phosphate–Regulated Hemolysin Gene (Phospholipase C) from *Pseudomonas aeruginosa*", *J. Bacteriol.* vol. 152, pp. 431–440 (1982).

Wion et al., "Human Lipoprotein Lipase Complementary DNA Sequence", *Science*, vol. 235, pp. 1638–1641 (1987).

Wohlfarth et al., "Molecular Genetics of the Extracellular Lipase of *Pseudomonas aeruginosa* PAO1", *J. General Microbiol.*, vol. 138, pp. 1325–1335 (1992).

Wohlfarth et al., "Chromosomal Mapping and Cloning of the Lipase Gene of *Pseudomonas aeruginosa*", *J. General Microbiol.*, vol. 134, pp. 433–440 (1988).

Yanisch–Perron et al., "Improved M13 Phage Cloning Vectors and Host Strains:Nucleotide Sequences of the M13mp18 and pUC19 Vectors", *Gene*, vol. 33, pp. 103–119 (1985).

Young and Davis, "Efficient Isolation of Genes by Using Antibody Probes", *Proc. Natl. Acad. Sci. USA*, vol. 80, pp. 1194–1198 (1983).

Zell and Fritz, "DNA Mismatch–repair in *Escherichia coli* Counteracting the Hydrolytic Deamination of 5–methyl–cytosine Residues", *EMBO Journal*, vol. 6, pp. 1809–1815 (1987).

Zyprian and Matzura, "Characterization of Signals Promoting Gene Expression on the *Staphylococcus aureus* Plasmid pUB110 . . . ", *DNA*, vol. 5, pp. 219–225 (1986).

Aoyama et al., "Cloning, Sequencing and Expression of the Lipase Gene from *Pseudomonas fragi* IFO–12049 in *E. coli*", *FEBS Letter*, vol. 242, pp. 36–40 (1988).

Gotz et al., *Nucleic Acids Research*, vol. 13, pp. 5895–5906 (1985).

Nilsson et al., *Nucleic Acids Res.*, vol. 11, pp. 8019–8030 (1983).

Freudl et al., *J. Biol. Chem.*, vol. 261, pp. 11355–11361 (1986).

Van Mourik, *J. Biol. Chem.*, vol. 260, pp. 11300–11306 (1985).

Ish–Horowicz et al., *Nucleic Acid Res.*, vol. 9, pp. 2989–2998 (1981).

Matsudaira, *J. Biol. Chem.*, vol. 262, pp. 10035–10038 (1987).

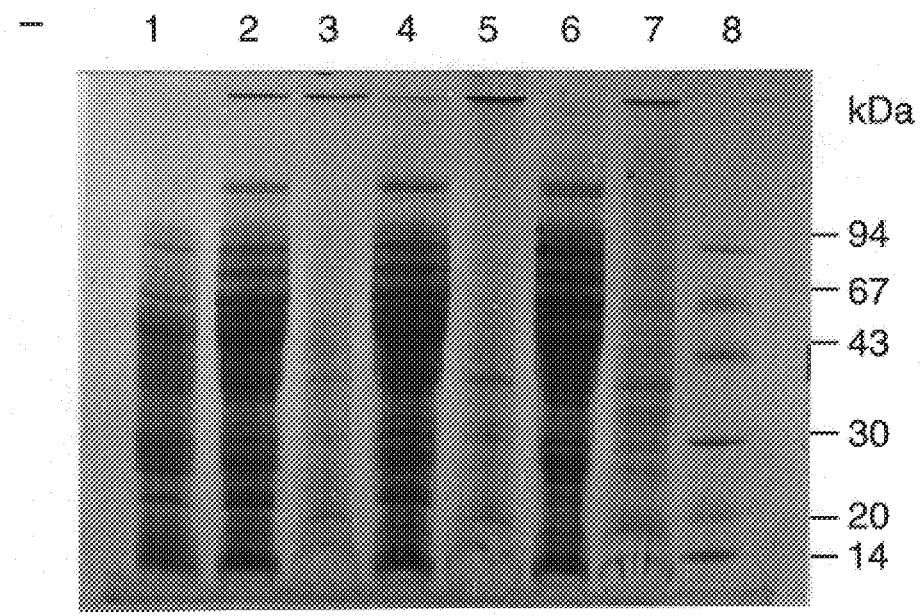
FIG._9A
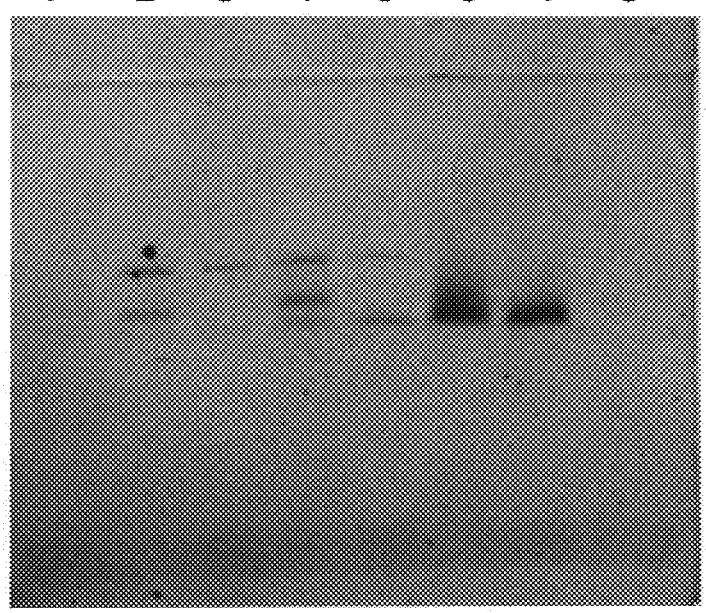
FIG._9B

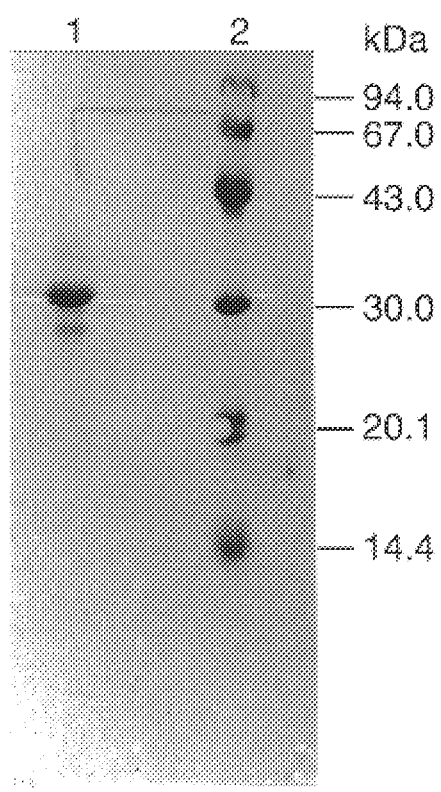
FIG._10

LIPASE M1

```
                                          30
ATG AAT AAC AAG AAA ACC CTG CTC GCC CTC TGC ATC GGC AGC AGT
 M   N   N   K   K   T   L   L   A   L   C   I   G   S   S

60              ↓                90
CTG CTG CTG TCC GGC CCA GCC GAA GCC GGC CTG TTC GGC TCC ACC
 L   L   L   S   G   P   A   E   A   G   L   F   G   S   T
                                     _____

120
GGC TAC ACC AAG ACC AAG TAC CCG ATC GTC CTG ACC CAC GGC ATG
 G   Y   T   K   T   K   Y   P   I   V   L   T   H   G   M
_____

150                               180
CTC GGC TTC GAC AGC ATC CTC GGC GTC GAC TAC TGG TAC GGC ATC
 L   G   F   D   S   I   L   G   V   D   Y   W   Y   G   I
_____

210
CCG TCC TCG CTG CGC TCC GAC GGC GCC AGC GTC TAC ATC ACC GAA
 P   S   S   L   R   S   D   G   A   S   V   Y   I   T   E 240                               270
GTC AGC CAG CTC AAC ACC TCC GAG CTG CGC GGC GAG GAG CTG CTG
 V   S   Q   L   N   T   S   E   L   R   G   E   E   L   L

300
GAG CAG GTG GAA GAG ATC GCC GCC ATC AGC GGC AAG GGC AAG GTC
 E   Q   V   E   E   I   A   A   I   S   G   K   G   K   V 330                               360
AAC CTG GTC GGC CAC AGC CAT GGC GGC CCG ACC GTC CGC TAC GTG
 N   L   V  [G   H   S   H   G]  G   P   T   V   R   Y   V
             A

GCC GCC GTA CGC CCG GAC CTG GTG GCC TCG GTG ACC AGC GTC GGC
 A   A   V   R   P   D   L   V   A   S   V   T   S   V   G 420                               450
GCC CCG CAC AAG GGC TCG GAC ACC GCC GAC TTC ATC CGC CAG ATC
 A   P   H   K   G   S   D   T   A   D   F   I   R   Q   I

480
CCC CGG GGC TCG GCC GGT GAG GCG ATA GTC GCC GGC ATC GTC AAC
 P   P   G   S   A   G   E   A   I   V   A   G   I   V   N
```

FIG.12A

```
                          510                                                  540
GGC CTG GGC GCG CTG ATC AAC TTC CTC TCC GGC AGC TCC AGC ACC
 G   L   G   A   L   I   N   F   L   S   G   S   S   S   T

570
AGC CCG CAG AAC GCC CTG GGC GCC CTC GAA TCG CTC AAC AGT GAG
 S   P   Q   N   A   L   G   A   L   E   S   L   N   S   E 600                                                      630
GGC GCC GCC GCC TTC AAC GCC AAG TAT CCG CAG GGC ATT CCG ACC
 G   A   A   A   F   N   A   K   Y   P   Q   G   I   P   T

660
AGT GCC TGC GGC GAA GGC GCC TAC AAG GTC AAT GGC GTC AGC TAC
 S   A   C   G   E   G   A   Y   K   V   N   G   V   S   Y 690                                                      720
TAC TCC TGG AGC GGC ACC AGC CCG CTG ACC AAT GTG CTC GAC GTC
 Y   S   W   S   G   T   S   P   L   T   N   V   L   D   V

750
AGC GAC CTG CTG CTG GGC GCC AGC TCG CTG ACC TTC GAC GAG CCC
 S   D   L   L   L   G   A   S   S   L   T   F   D   E   P 780                                                  810
AAC GAC GGC CTG GTC GGG CGC TGC AGC TCG CAC CTG GGC AAG GTG
 N   D   G   L   V   G   R   C   S   S   H   L   G   K   V

840
ATC CGC GAC GAC TAC CGG ATG AAC CAC CTC GAC GAG GTC AAC CAG
 I   R   D   D   Y   R   M   N   H   L   D   E   V   N   Q 870                                      900
ACC TTC GGC CTG ACC AGC CTG TTC GAG ACC GAC CCG GTC ACC GTG
 T   F   G   L   T   S   L   F   E   T   D   P   V   T   V

930
TAC CGC CAG CAG GCC AAC CGC CTC AAA CTG GCC GGC CTC TGA
 Y   R   Q   Q   A   N   R   L   K   L   A   G   L   *
```

FIG. 12B

LIPASE PA01

```
                                    30
GTC GAC TAC TGG TTC GGC ATT TCC CAG CGC CTT GCG CGT GAC GGT
 V   D   Y   W   F   G   I   S   Q   R   L   A   R   D   G 60                                  90
GCC CAG GTC TAC GTC ACC GAA TGT CAG CCA GTT GGA CAC TCG GAA
 A   Q   V   Y   V   T   E   C   Q   P   V   G   H   S   E

120
GTC CGC GGC GAG CAG TTG CTG CAA CAG GTG GAG GAA ATC GTC GCC
 V   R   G   E   Q   L   L   Q   Q   V   E   E   I   V   A 150                                         180
CTC AGC GGC CAG CCC AAG GTC AAC CTG ATC GGC CAC AGC CAC GGC
 L   S   G   Q   P   K   V   N   L   I  [G   H   S   H   G]
                                                A

210
GGG CCG ACC ATC CGC TAC GTC GCC GCC GTA CGT CCC GAC CTG ATC
 G   P   T   I   R   Y   V   A   A   V   R   P   D   L   I 240                                     270
GCT TCC GCC ACC AGC GTC GGC GCC CCG CAC AAG GGT TCG GAC ACC
 A   S   A   T   S   V   G   A   P   H   K   G   S   D   T

300
GCC GAC TTC CTG CGC CAG ATC CCA CCG GGT TCG GCC GGC GAG GCA
 A   D   F   L   R   Q   I   P   P   G   S   A   G   E   A 330                                     360
GTC CTC TCC GGG CTG GTC AAC AGC CTC GGC GCG CTG ATC AGC TTC
 V   L   S   G   L   V   N   S   L   G   A   L   I   S   F

390
CTT TCC AGC GGC AGC ACC GGT ACG CAG AAT TCA CTG GGC TCG CTG
 L   S   S   G   S   T   G   T   Q   N   S   L   G   S   L
```

FIG.14A

```
                      420                                              450
GAG TCG CTG AAC AGC GAG GGT GCC GCG CGC TTC AAC GCC AAG TAC
 E   S   L   N   S   E   G   A   A   R   F   N   A   K   Y

480
CCG CAG GGC ATC CCC ACC TCG GCC TGC GGC GAA GGC GCC TAC AAG
 P   Q   G   I   P   T   S   A   C   G   E   G   A   Y   K 510                                      540
GTC AAC GGC GTG AGC TAT TAC TCC TGG AGC GGT TCC TCG CCG CTG
 V   N   G   V   S   Y   Y   S   W   S   G   S   S   P   L

570
ACC AAC TTC CTC GAT CCG AGC GAC GCC TTC CTC GGC GCC TCG TCG
 T   N   F   L   D   P   S   D   A   F   L   G   A   S   S 600                                          630
CTG ACC TTC AAG AAC GGC ACC GCC AAC GAC GGC CTG GTC GGC ACC
 L   T   F   K   N   G   T   A   N   D   G   L   V   G   T

660
TGC AGT TCG CAC CTG GGC ATG GTG ATC CGC GAC AAC TAC CGG ATG
 C   S   S   H   L   G   M   V   I   R   D   N   Y   R   M 690                                      720
AAC CAC CTG GAC GAG GTG AAC CAG GTC TTC GGC CTC ACC AGC CTG
 N   H   L   D   E   V   N   Q   V   F   G   L   T   S   L

750
TTC GAG ACC AGC CCG GTC AGC GTC TAC CGC CAG CAC GCC AAC CGC
 F   E   T   S   P   V   S   V   Y   R   Q   H   A   N   R

780
CTG AAG AAC GCC AGC CTG TAG
 L   K   N   A   S   L   *
```

FIG.14B

FIG. 16
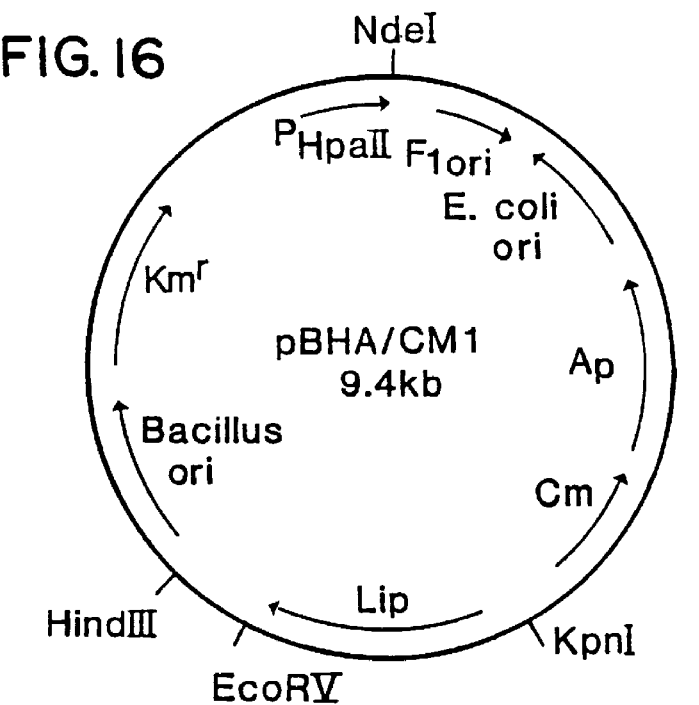
Introduction of NdeI site on ATG initiation codon of M1 lipase gene
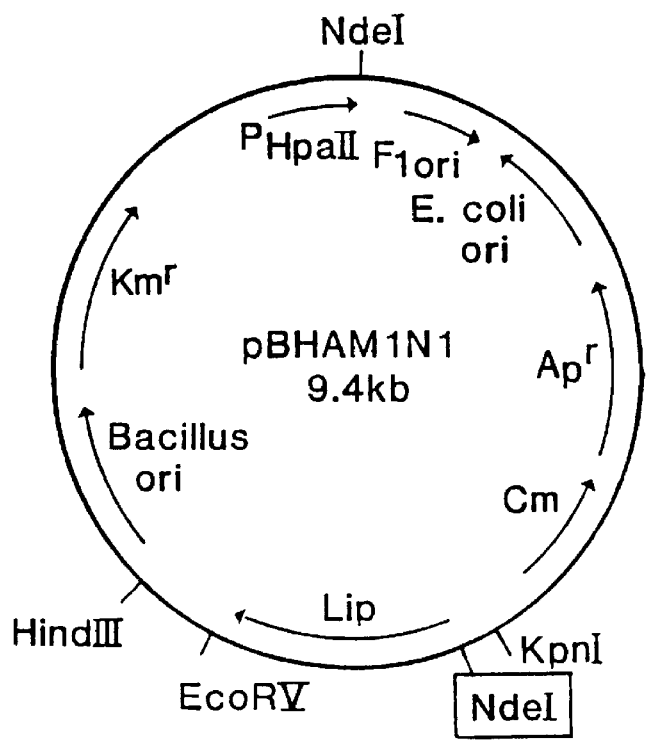

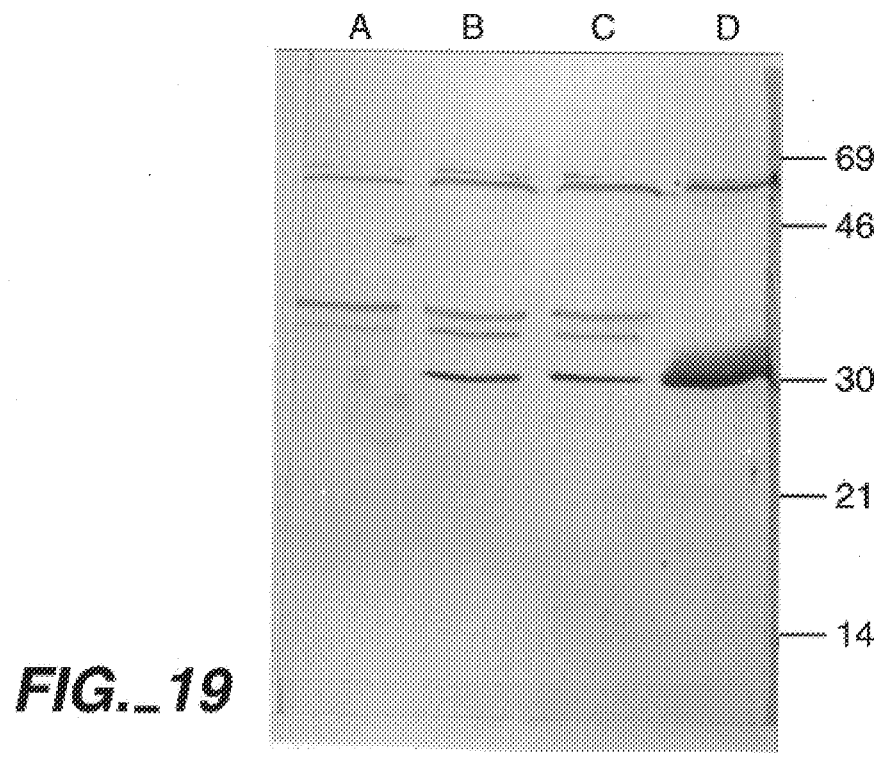
FIG._19
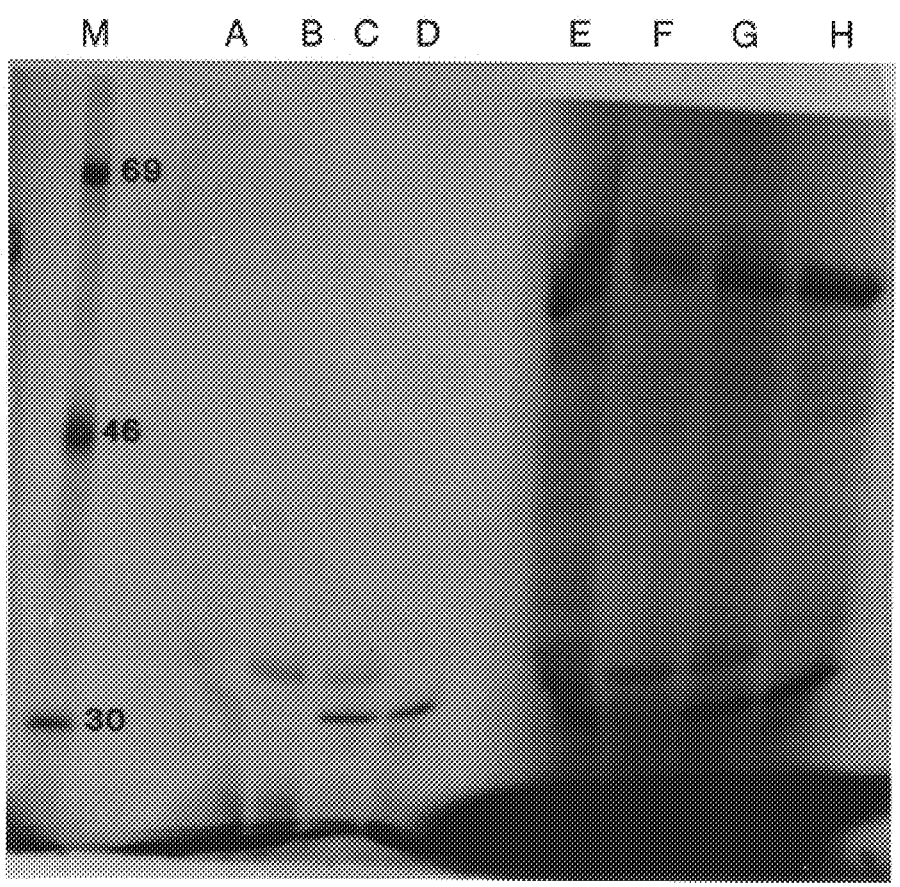
FIG._21

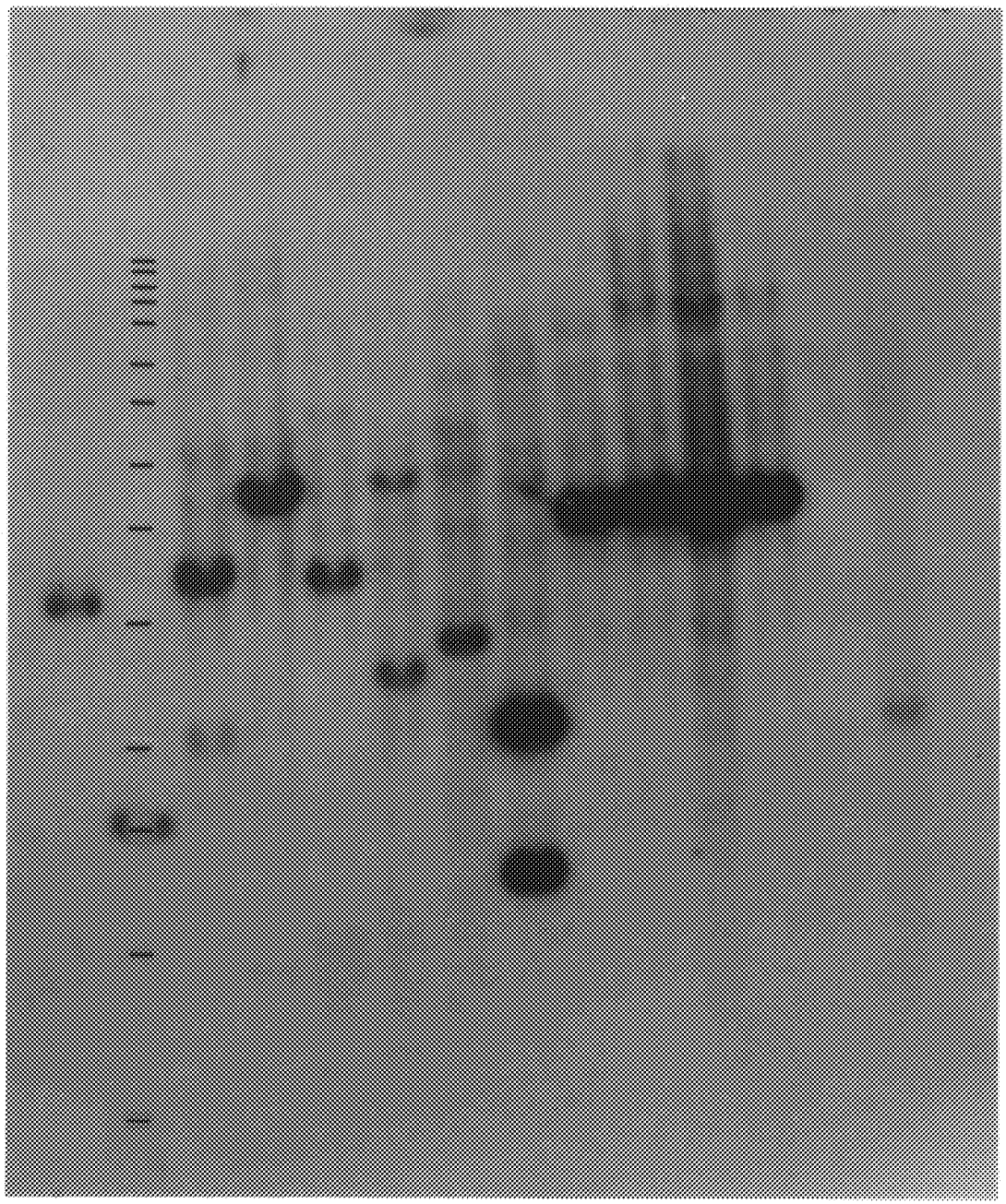
FIG._22A

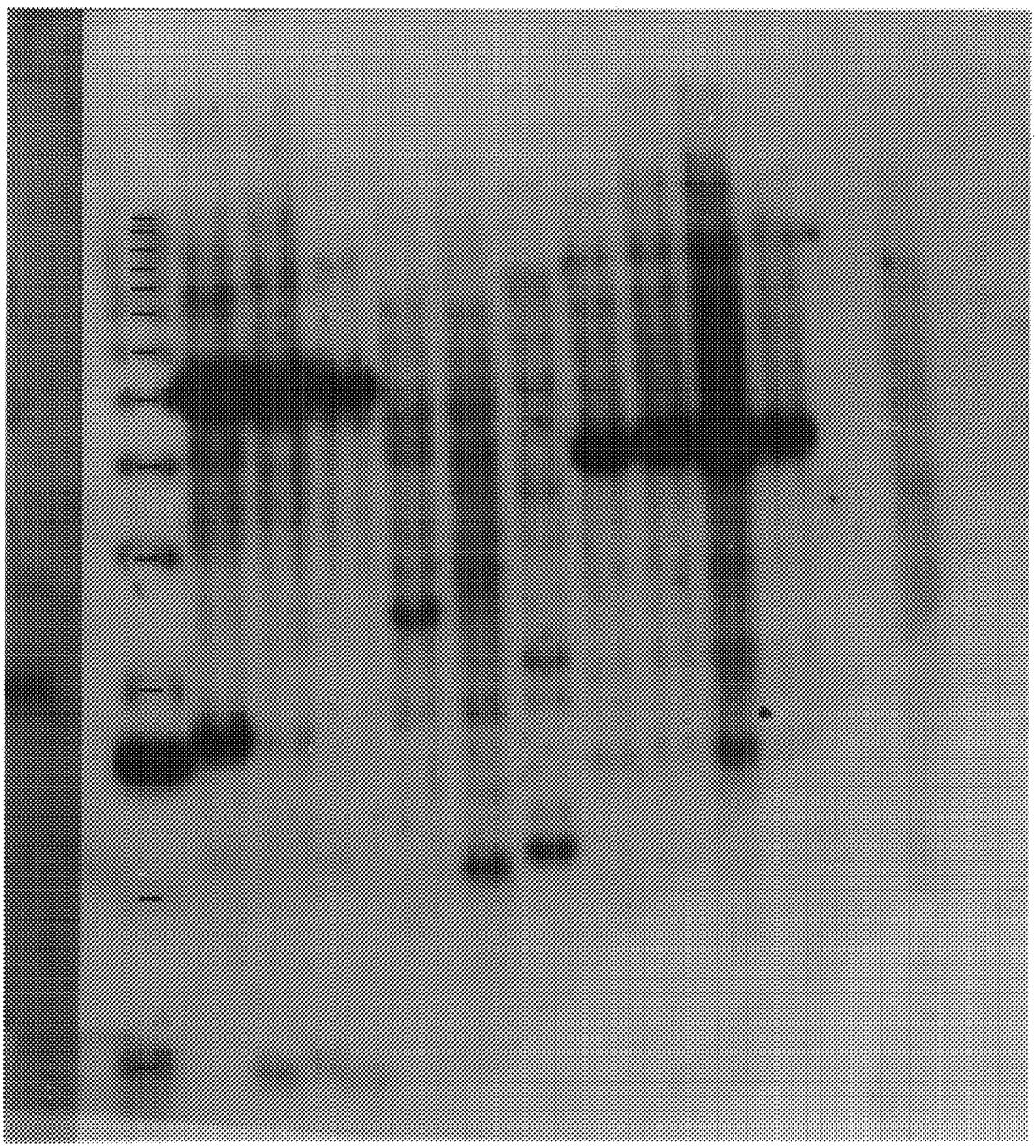
FIG._22B

METHOD FOR PRODUCING LIPOLYTIC ENZYMES USING TRANSFORMED PSEUDOMONAS

CROSS REFERENCE TO RELATED APPLICATIONS

This application is a division of U.S. application Ser. No. 07/415,142, filed Sep. 25, 1989, now U.S. Pat. No. 5,278,066, which is a continuation-in-part of U.S. application Ser. No. 07/154,182, filed Feb. 9, 1988, now abandoned, which is a continuation-in-part of U.S. application Ser. No. 07/034,418, now U.S. Pat. No. 4,933,287.

TECHNICAL FIELD

This invention relates to the preparation, by recombinant DNA technology, of enzymes for the enzymatic degradation of fatty materials, specifically lipolytic enzymes which have characteristics which make them suitable for use as detergent additives.

BACKGROUND

A special problem associated with laundry cleaning is the removal of stains of a fatty nature. Currently, fat-containing dirt is emulsified and removed using a combination of elevated temperature and high alkalinity. However, there is a recent strong tendency toward the use of relatively low washing temperatures, namely about 40° C. or lower, conditions particularly unsuited for fatty stain removal. There is therefore a need for detergent additives which are effective at the lower washing temperatures, stable in high alkaline detergent solutions and stable under storing conditions in both solid and liquid detergent compositions. A group of enzymes which hydrolize triglycerides are lipases (E.C. 3.1.1.3). Lipases are widely distributed, occurring in many different prokaryotic organisms, as well as eukaryotic cells. Depending upon the source of the enzyme, substrate specificity as well as other characteristics including stability under various conditions, varies widely. Lipases have been used in detergent compositions, however those used exhibited low cleaning efficiency under washing conditions and in addition, did not meet the stability requirements for detergent use.

Lipolytic enzymes which are capable of exhibiting lipase activity under modern washing conditions, i.e., they are stable and effective at high detergent concentrations, at high pH and at low washing temperatures, are produced by certain strains belonging to the species of *Pseudomonas pseudoalcaligenes, Pseudomonas stutzeri* and *Acinetobacter calcoaceticus* (see European Patent Application EP-A-0218272). However, these species are potentially pathogenic for plants and animals, and few data are available on the fermentation conditions required for an effective production process for lipases using these microorganisms.

It is therefore desirable to develop an efficient and safe way to produce lipolytic enzymes having the desired characteristics for detergent additives. Moreover, it is desirable that the lipases be secreted by the host organism so that the enzyme may be recovered directly from the extracellular fluid of the fermentation mixture.

RELEVANT LITERATURE

For lipases produced by Pseudomonas species it is known that the culture conditions strongly influence the final localization of these enzymes (Sugiura, In: "Lipases", eds. B. Borgstrom and H. L. Brockman (1984) pp. 505–523, Elsevier, Amsterdam). Problems are often encountered in obtaining efficient expression of heterologous genes in microorganisms, including incorrect folding of the proteins formed, protein degradation and improper localization of the products. Harris, In: "Genetic Engineering", Vol. 4 (1983), Academic Press, New York. In *E. coli* the use of secretion-cloning vectors generally enables the transport of heterologous gene products into the periplasmic space and products are only occasionally found in the culture medium; Lunn et al., Current Topics in Microbiol. and Immunol. 125 (1986) 59–74. When using *E. coli* as the host cell, cloned microbial lipases, described by Gotz et al., Nucleic Acids Res. 13 (1985) 5895–5906, Kugimiya et al., Biochem. Biophys. Res. Commun. 141 (1986) 185–190 and Odera et al., J. Ferment. Technol. 64 (1986) 363–371, are poorly secreted into the culture medium.

Wohlfarth and Winkler, J. Gen. Microbiol. 134 (1988) 433–440, report on the physiological characterization of newly isolated lipase-deficient mutants from *Pseudomonas aeruginosa* strain PAO 2302 and on the chromosomal mapping and cloning of the corresponding gene.

Bacillus species, in particular *Bacillus subtilis* strains have been used with varying degrees of success as host strains for the expression of both foreign and endogenous genes and for the secretion of the encoded protein products. For a review, see for example Sarvas, Current Topics in Microbiology and Immunology 125 (1986) 103–125, H. C. Wu and P. C. Tai, eds., Springer Verlag; also see Himeno et al., F.E.M.S. Microbiol. Letters 35 (1986) 17–21.

U.S. Pat. No. 3,950,277 and British Patent Specification No. 1,442,418 disclose lipase enzymes combined with an activator and calcium and/or magnesium ions, respectively, which are utilized to pre-soak soiled fabrics and to remove triglyceride stains and soils from polyester or polyester/cotton fabric blends, respectively. Suitable microbial lipases disclosed include those derived from Pseudomonas, Aspergillus, Pneumococcus, Staphylococcus, *Mycobacterium tuberculosis, Mycotorula lipolytica* and Sclerotinia.

British Patent Specification No. 1,372,034 discloses a detergent composition comprising a bacterial lipase produced by *Pseudomonas stutzeri* strain ATCC 19154. The patent further discloses that the preferred lipolytic enzymes should have a pH optimum between 6 and 10, and should be active in said range, preferably between 7 and 9. (This presumed *Pseudomonas stutzeri* strain has been reclassified as *Pseudomonas aeruginosa*).

European Patent Application (EP-A) 0130064 discloses an enzymatic detergent additive comprising a lipase isolated from *Fusarium oxysporum* which has a higher lipolytic cleaning efficiency than conventional lipases. Lipolytic detergent additives were also disclosed in, e.g., British Patent Specification No. 1,293,613 and Canadian Patent No. 835,343.

European Patent Applications EP-A-0205208 and EP-A-0206396 disclose use of Pseudomonas and Chromobacter lipases in detergents. For a comprehensive review article on lipases as detergent additives, see Andree et al., J. Appl. Biochem. 2 (1980) 218–229.

SUMMARY OF THE INVENTION

Novel compositions comprising transformed microbial cells, and methods for their preparation, are provided which produce lipolytic enzymes suitable for use in detergent compositions. Host microbial cells are transformed using expression cassettes comprising a DNA sequence encoding a lipolytic enzyme which is active at alkaline pH and stable under laundry washing conditions. Methods for preparation of the lipolytic enzymes include cloning and expression in microbial systems and screening on the basis of DNA homology.

Two novel DNA sequences are also provided, said DNA sequences comprising a gene encoding a lipolytic enzyme derived from a *Pseudomonas pseudoalcaligenes* strain and a *Pseudomonas aeruginosa* strain, respectively.

Of particular interest for the production of lipase are lipase genes derived from certain Pseudomonas species.

The position at which partially Sau3A digested chromosomal DNA of *Pseudomonas stutzeri* Thai IV 17-1 (CBS 461.85) was ligated to pUN121 is indicated by BclI/Sau3A. The position of the gene encoding lipolytic activity is indicated by a dashed line.

Figure 2:
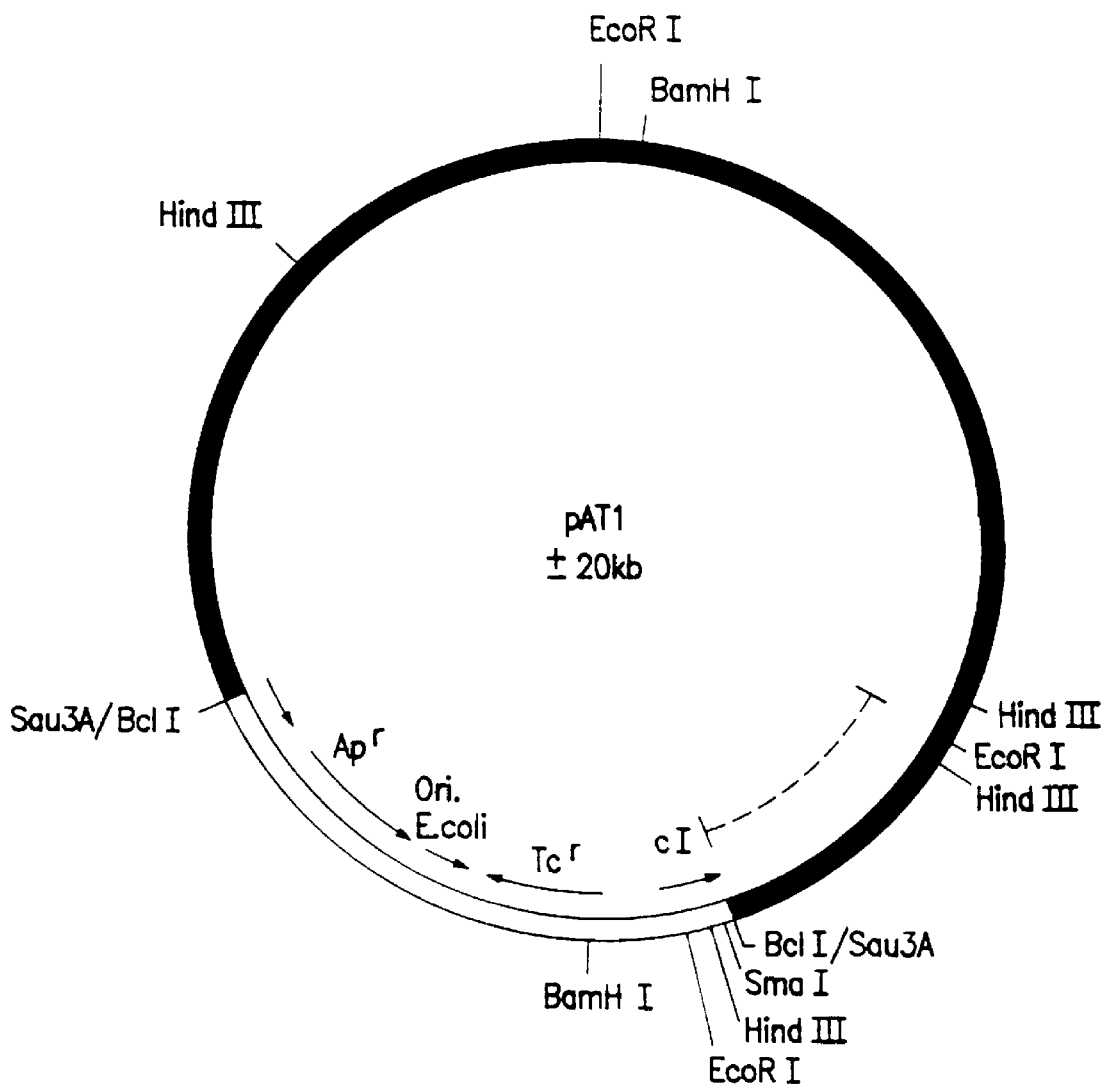
FIG. 2: Restiction map of pAT1. A number of restriction enzyme recognition sites have been determined in plasmid pAT1.
▢: pUN121 vector DNA
■: Thai IV 17-1 DNA insert
Symbols used are:
Ori *E. coli*: *E. coli* origin of replication
$Ap^r$: the pUN121 gene encoding ampicillin resistance;
$Tc^r$: the pUN121 gene encoding tetracycline resistance;
cI: the bacteriophage lambda gene encoding the cI repressor.
Figure 3:
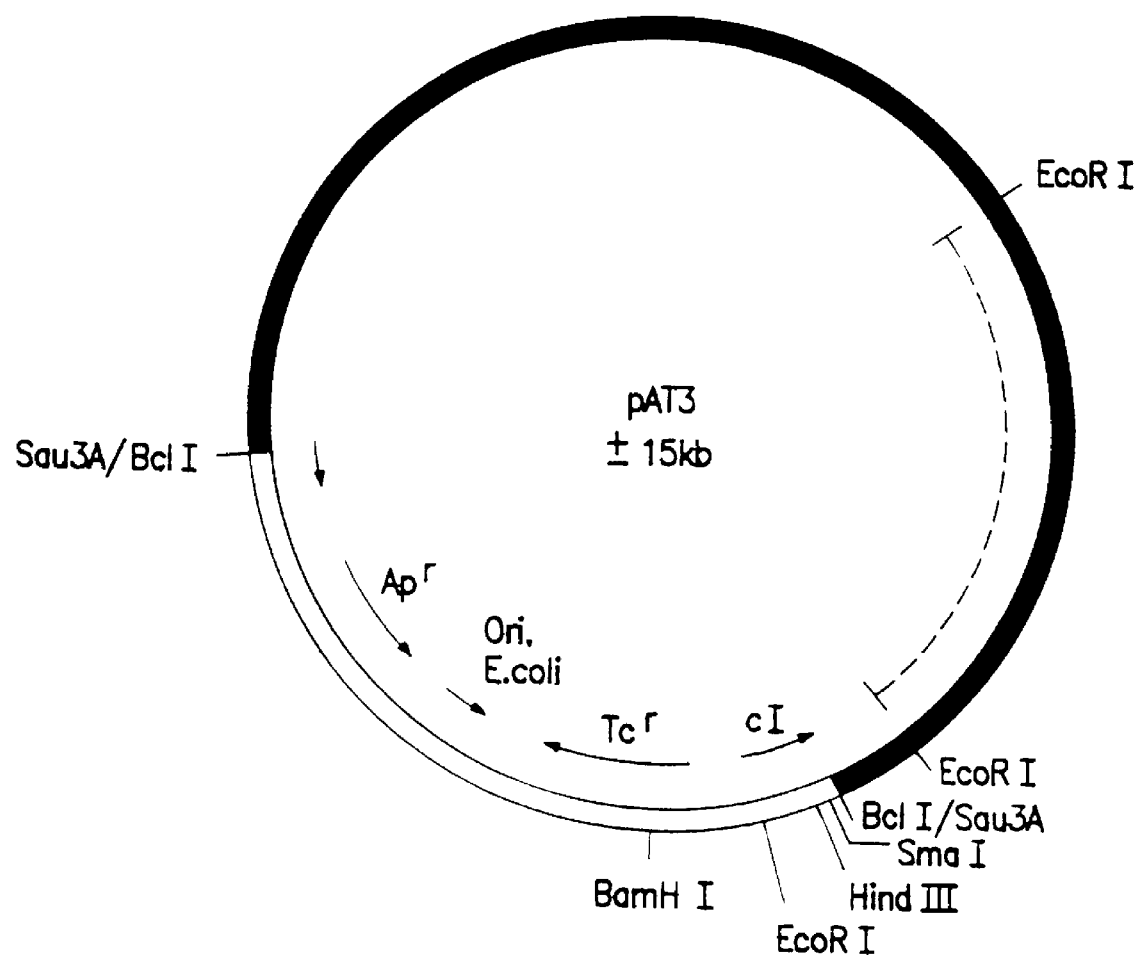

FIG. 3: Restriction map of pAT3. The symbols are the same as used in FIG. 2.

Figure 4:
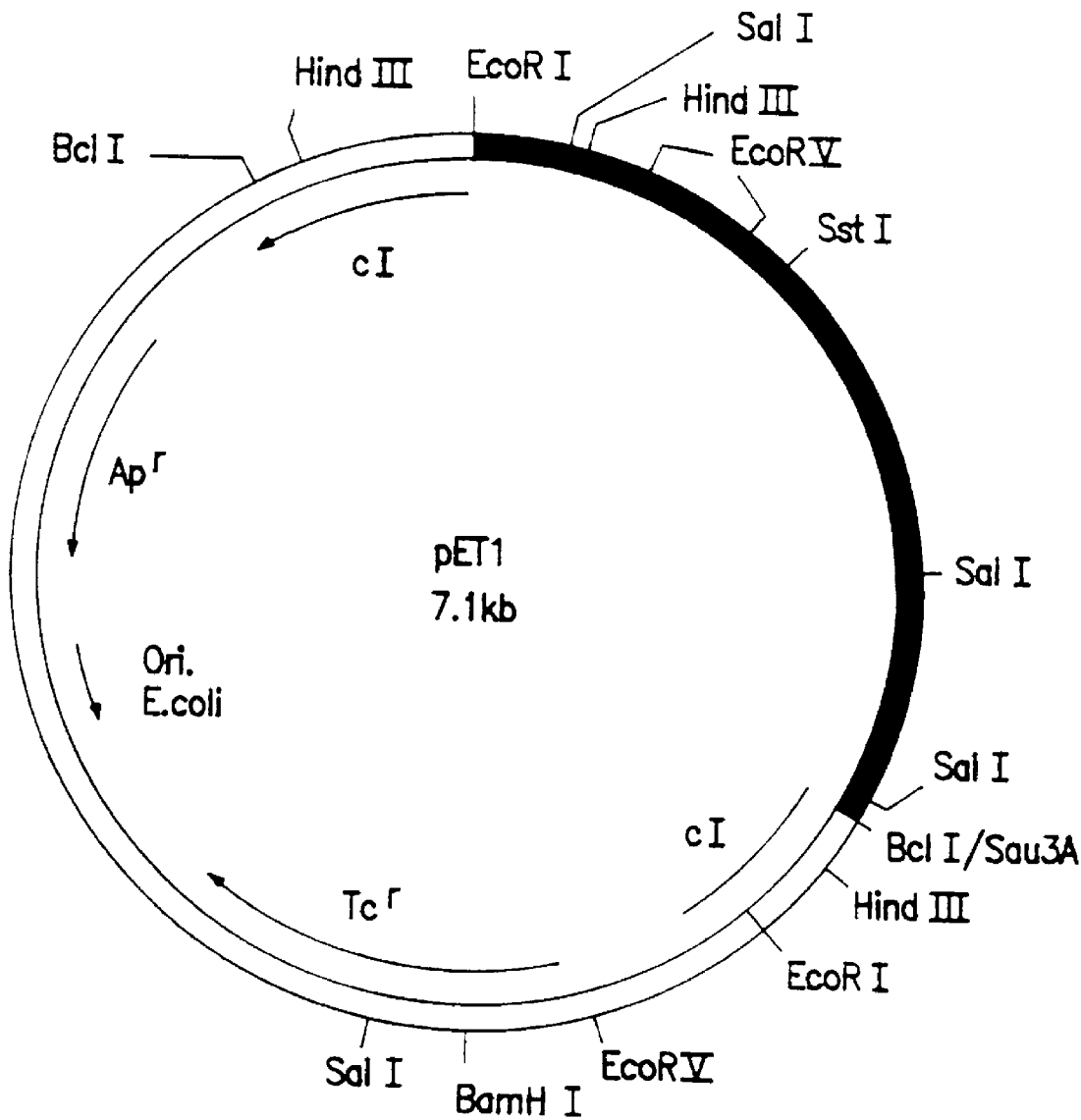

FIG. 4: Restriction map of pET1. The symbols are the same as used in FIG. 2.

Figure 5:
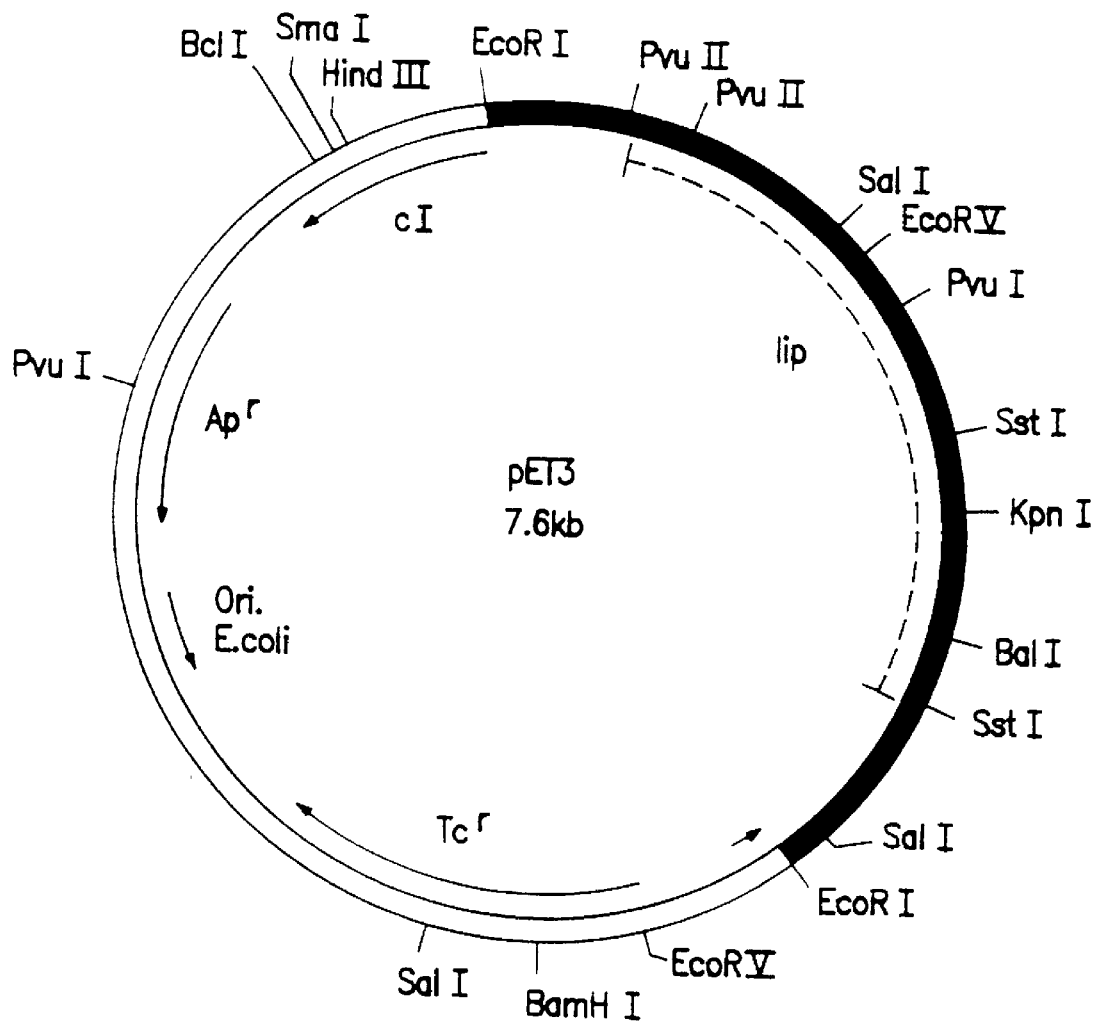

FIG. 5: Restriction map of pET3. The symbols are the same as used in FIG. 2.

Figure 6:
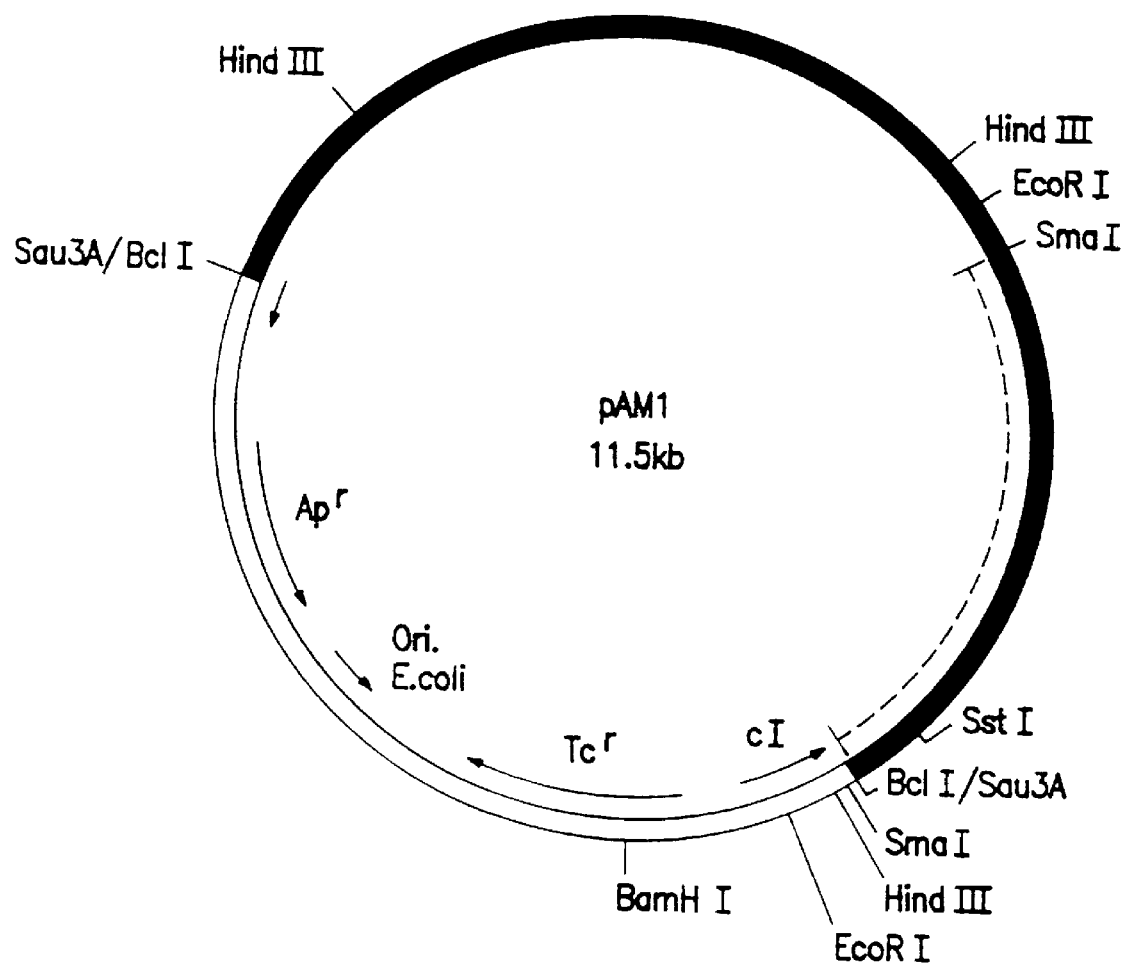

FIG. 6: Restriction map of pAM1. The symbols are the same as used in FIG. 2.

Figure 7:
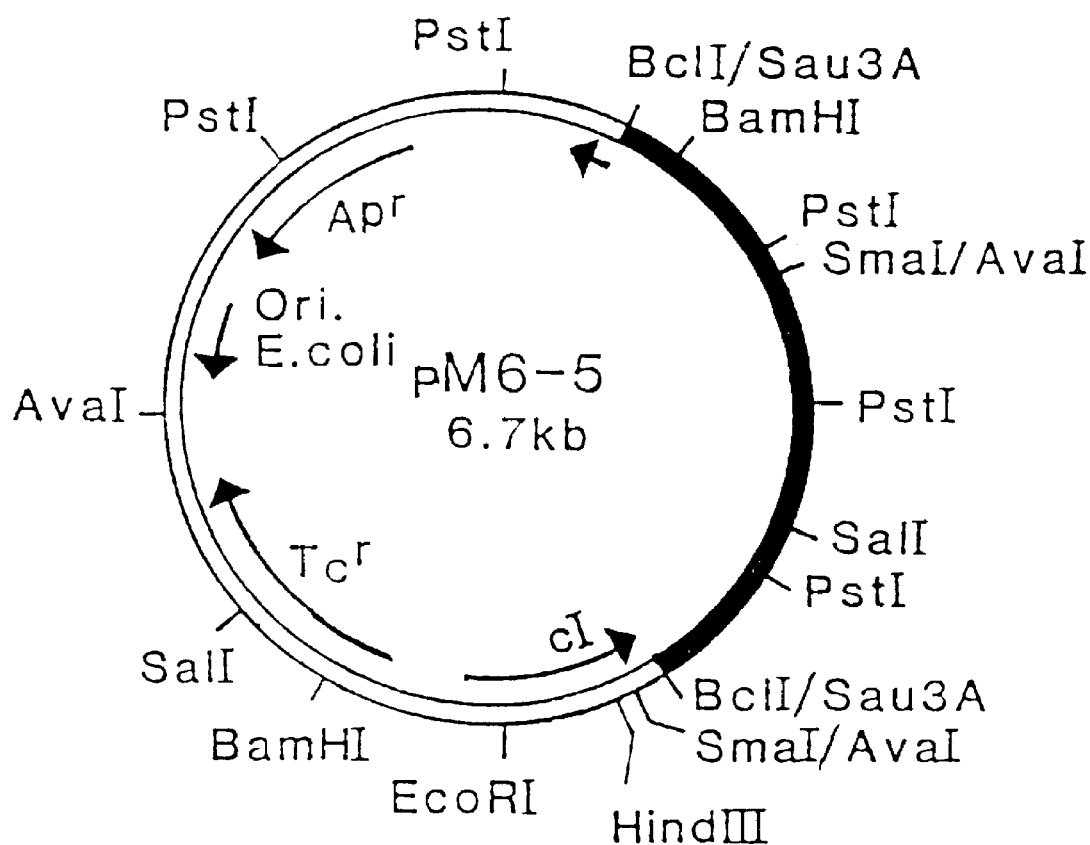

FIG. 7: Restriction map of pM6-5. The symbols are the same as used in FIG. 2.

Figure 8:
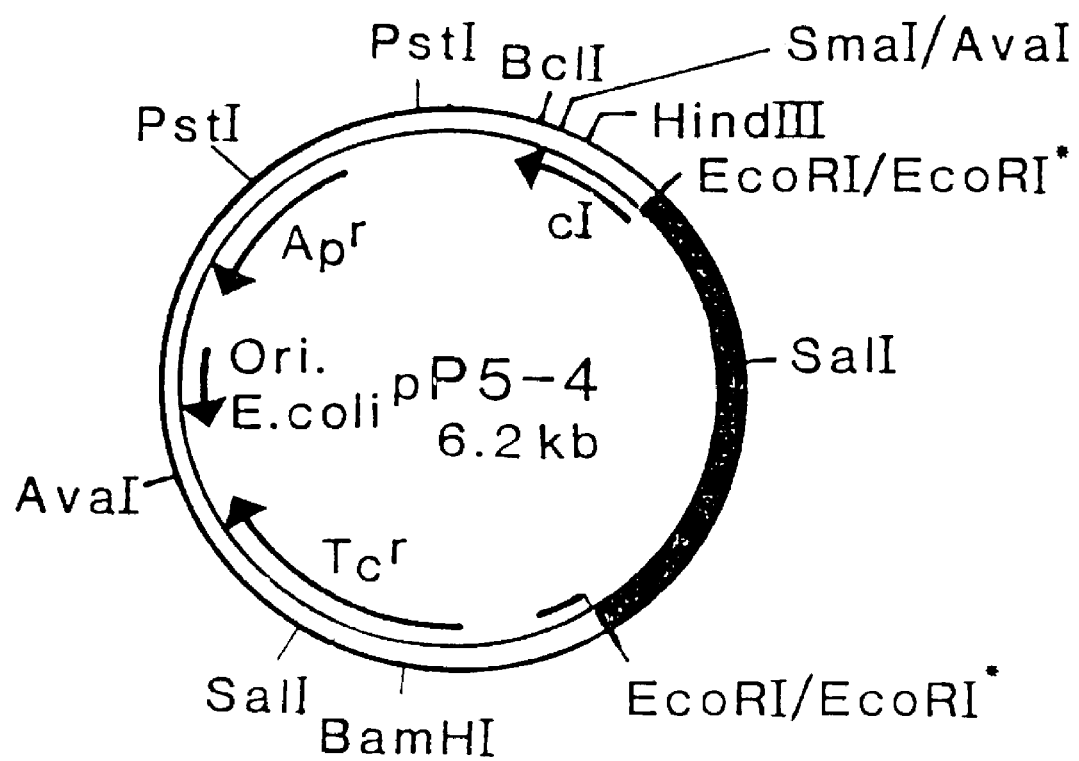

FIG. 8: Restiction map of pP5-4. The symbols are the same as used in FIG. 2. The position at which partially EcoRI* digested chromosomal DNA of *Acinetobacter calcoaceticus* GR V-39 (CBS 460.85) was ligated to pUN121 is indicated by EcoRI/EcoRI*.

FIG. 9: A SDS 10–15% gradient Phastgel (Pharmacia)

FIG. 9A: after staining with Coomassie Brilliant Blue.

FIG. 9B: after staining with β-naphthyl acetate/Fast Blue BB.

Lane 1: lysate from *E. coli* JM101 hsdS recA strain harbouring pUN121 heated with SDS for 10 min at 95° C.
Lane 2: lysate from *E. coli* JM101 hsdS recA strain harbouring pET3 heated with SDS for 10 min at 95° C.
Lane 3: culture supernatant from *P. stutzeri* Thai IV 17-1 strain heated with SDS for 10 min at 95° C.
Lane 4: the same sample as in lane 2 but heated with SDS for 5 min at 95° C.
Lane 5: the same sample as in lane 3 but heated with SDS for 5 min at 95° C.
Lane 6: the same sample as in lane 2 but incubated with SDS for 10 min at room temperature.
Lane 7: the same sample as in lane 3 but incubated with SDS for 10 min at room temperature.
Lane 8: low molecular weight protein markers from Pharmacia.

FIG. 10: SDS 13% polyacrylamide gel after staining with Coomassie Brilliant Blue.

Lane 1: purified M-1 lipase
Lane 2: low molecular weight protein markers (Pharmacia).

Figure 11:
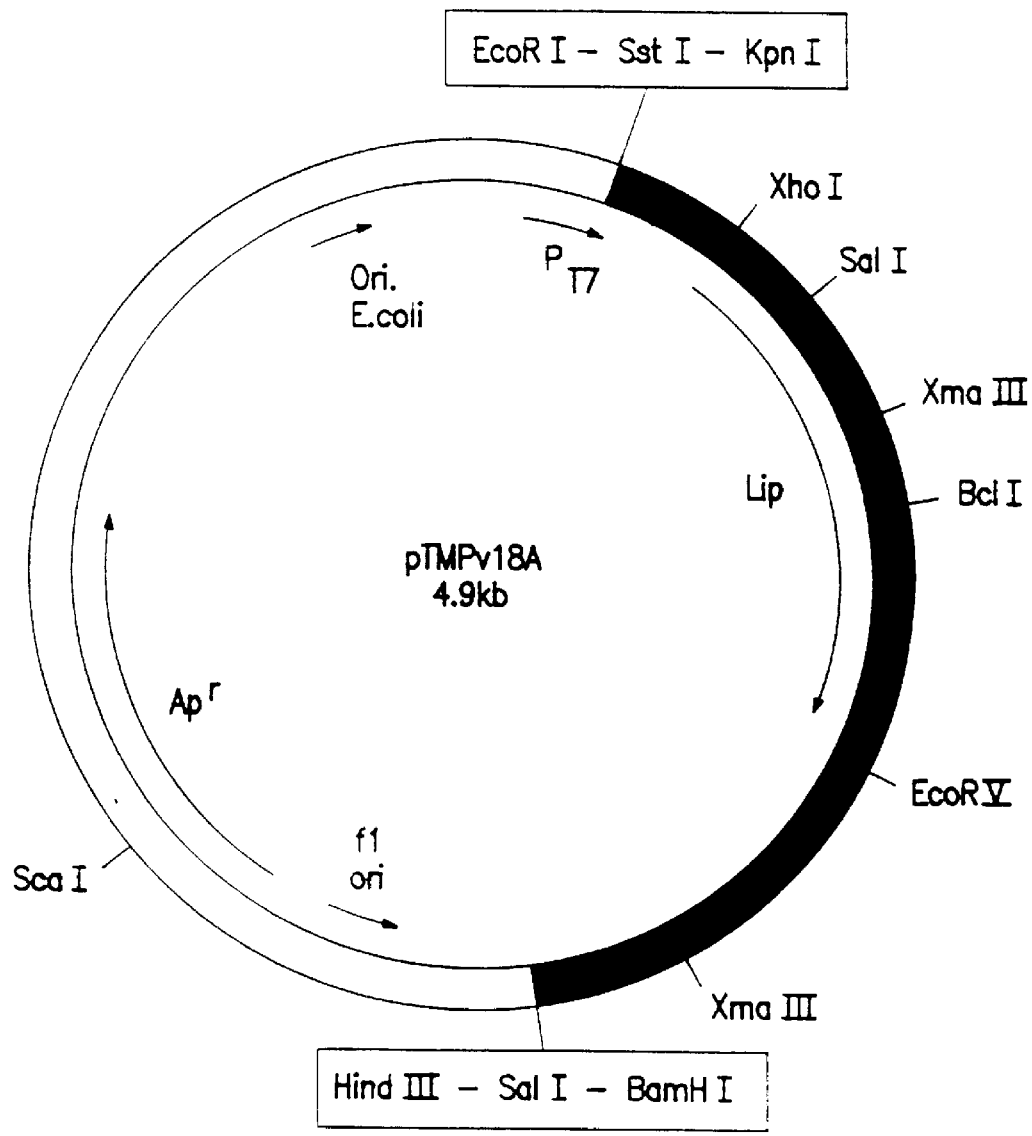

FIG. 11: Restriction map of pTMPv18A.
▢: pTZ18R vector DNA
■: M-1 DNA insert
Symbols used are:
Ori *E. coli*: *E. coli* origin of replication derived from pBR322 vector
fl ori: origin of replication from the filamentous bacteriophage fl
$P_{T7}$: promoter of the bacteriophage T7 for preparing in vitro transcripts
$Ap^r$: gene encoding ampicillin resistance
Lip: gene encoding the M-1 lipase.

FIG. 12 shows the nucleotide sequence (i.e. the first 942 nucleotides) of the M-1 lipase gene and the derived amino acid sequence of the M-1 lipase. The termination codon TGA is indicated by an asterisk. The A box represents the active center of the lipase protein. The arrow indicates the putative signal peptidase cleavage site. The amino terminal sequence of the mature lipase protein is underlined.

Figure 13:
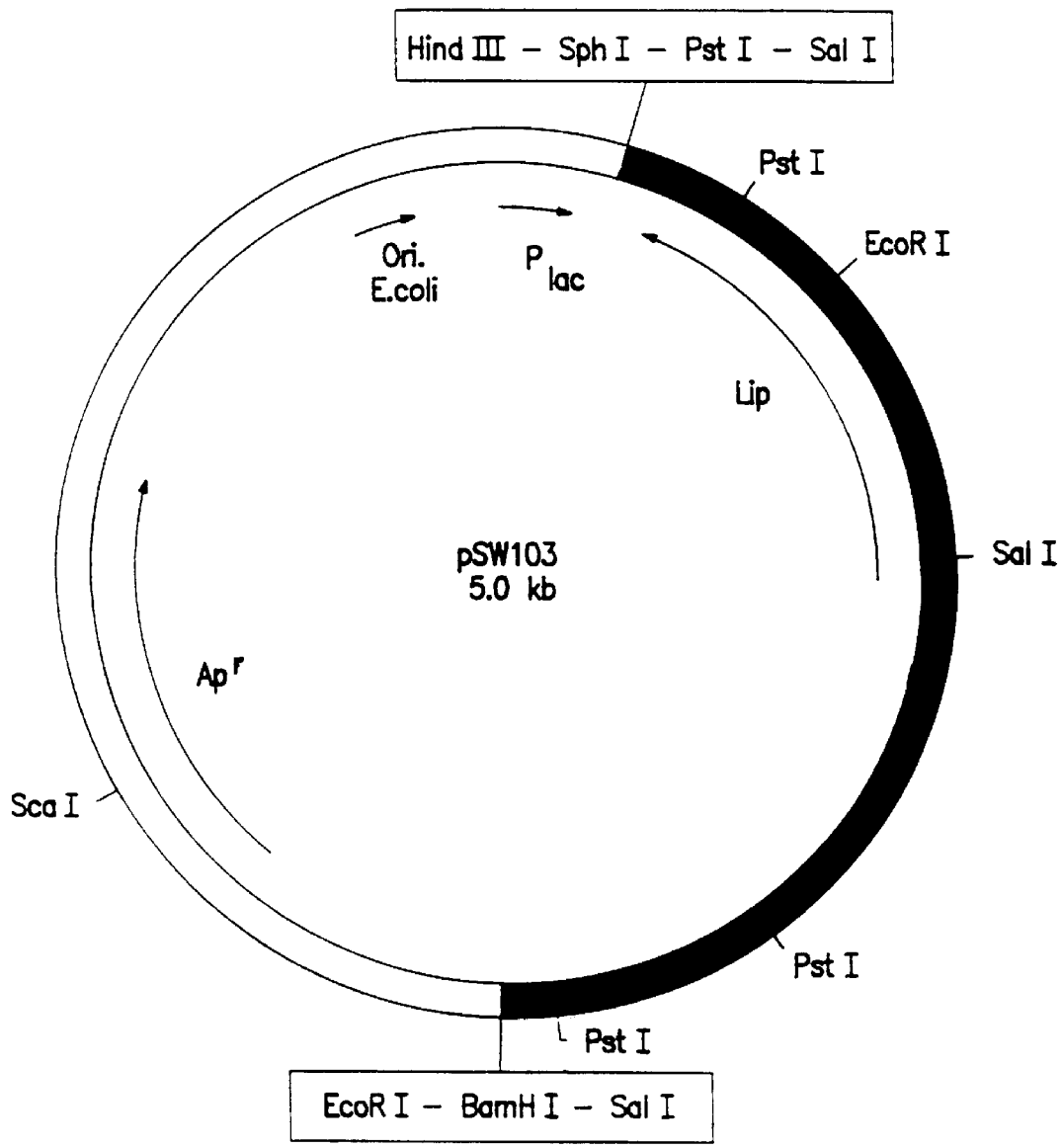

FIG. 13: Restriction map of pSW103
▢: pUC19 vector DNA
■: PAO 1 DNA insert
Symbols used are:
Ori *E. coli*: *E. coli* origin of replication derived from pBR322 vector
$P_{lac}$: promoter of the *E. coli* lac operon
$Ap^r$: gene encoding ampicillin resistance
Lip: gene encoding the PAO 1 lipase.

FIG. 14: Partial nucleotide sequence of the PAO lipase gene (i.e. from the internal SalI site) and derived amino acid sequence of the PAO lipase. The termination codon TAG is indicated by an asterisk. The A box represents the active center of the lipase protein.

Figure 15:
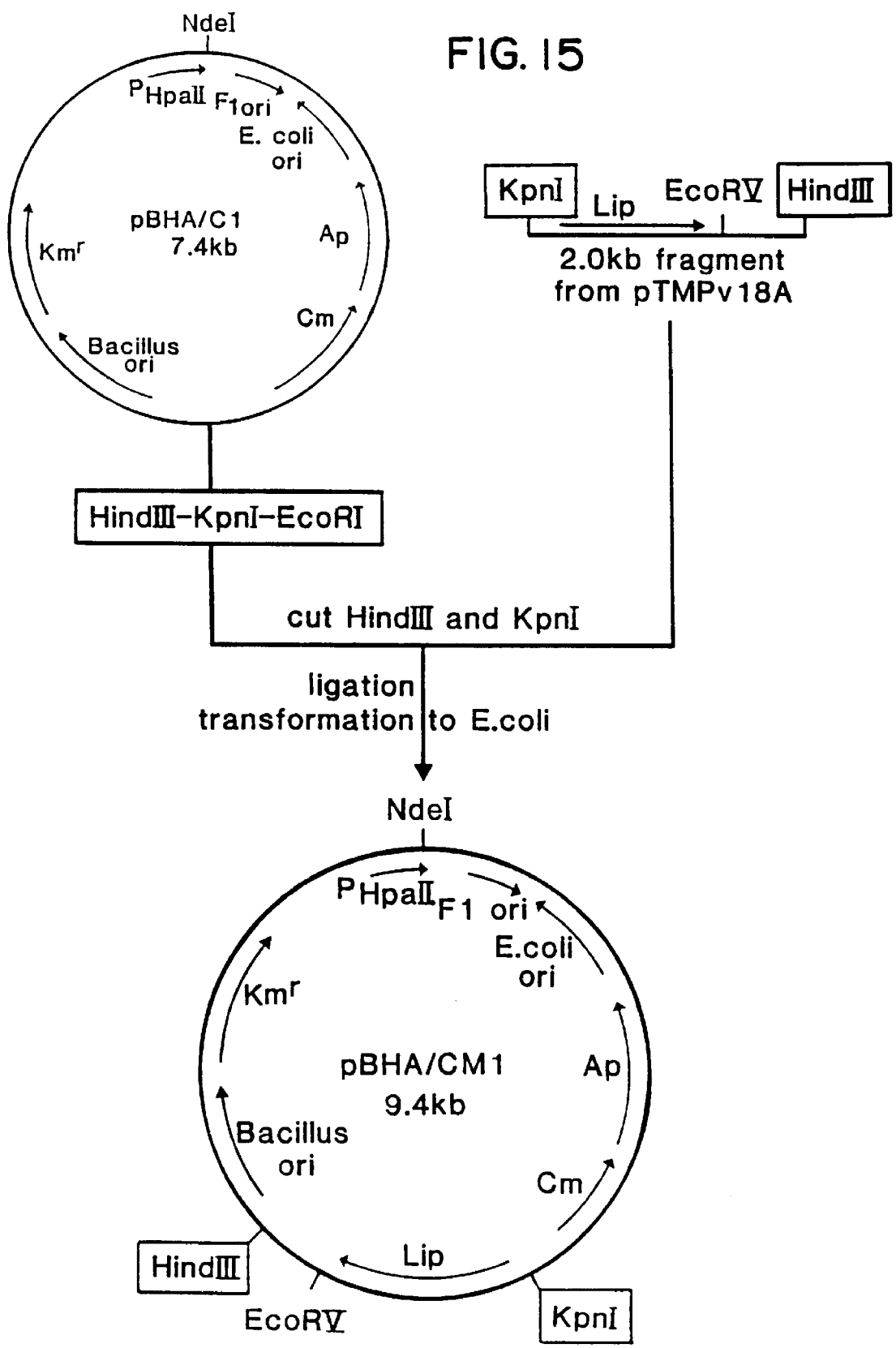

FIG. 15: The construction of the plasmids pBHAM1 and pBHCM1. Symbols used are:
Bacillus ori: Bacillus origin of replication
$Km^r$: the pUB110 gene encoding neomycin resistance
Cm: the Tn9 transposon gene encoding chloramphenicol resistance.
$P_{HpaII}$: HpaII promoter of plasmid pUB110. Other symbols as in FIG. 11.

FIG. 16 shows the construction of plasmid pBHAM1N1. The symbols are the same as used in FIG. 15.

Figure 17:
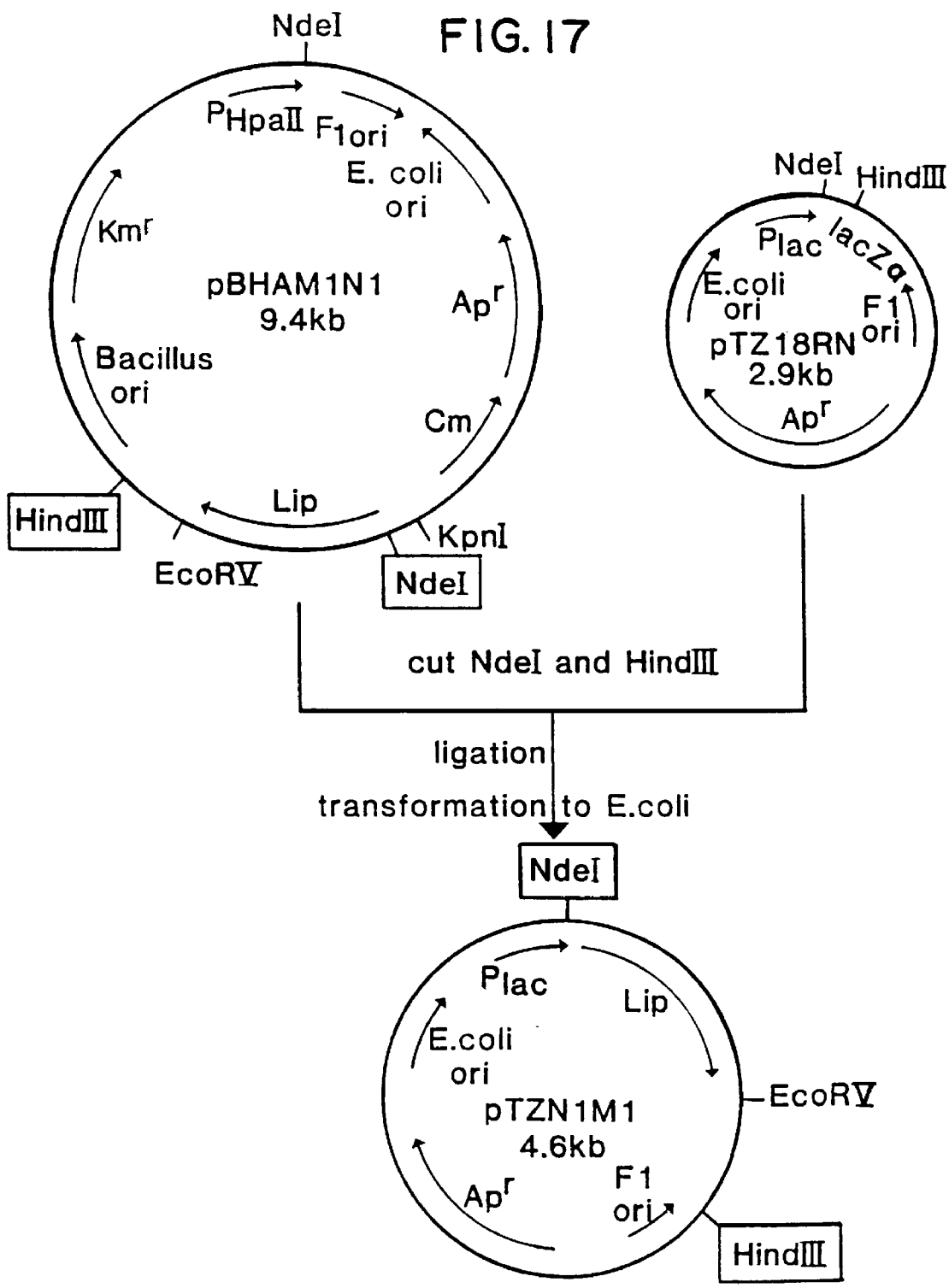

FIG. 17 illustrates the construction of plasmid pTZN1M1. Symbols used are:
lac Zα: N-terminal part of LacZ gene encoding the α-domain of β-galactosidase.
$P_{lac}$: promoter of the *E. coli* lac operon. Other symbols as in FIG. 11.

Figure 18:
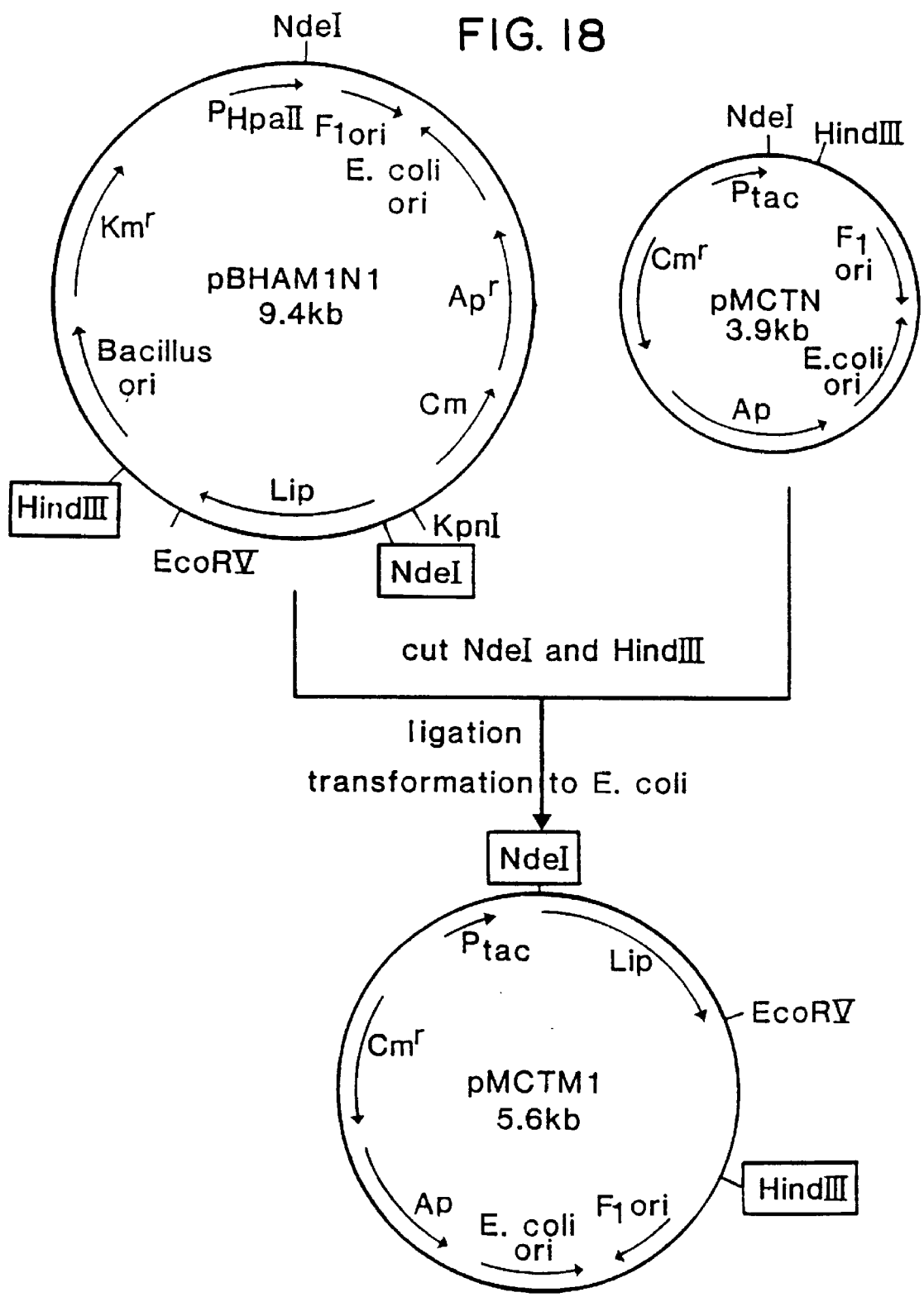

FIG. 18 shows the construction of plasmid pMCTM1. Symbols used are:
$Cm^r$: gene encoding chloramphenicol resistance
$P_{tac}$: hybrid trp-lac *E. coli* promoter. Other symbols as in FIGS. 11 and 15.

FIG. 19: Immunoblot detection of M-1 lipase protein produced by transformed *E. coli* cells.
Lanes A–D contain periplasmic fractions of *E. coli* cells harbouring the following constructs:
Lane A: pTZ18RN
Lane B: pTZN1M1
Lane C: pMCTM1
Lane D: purified M-1 lipase from *Pseudomonas pseudoalcaligenes* strain M-1. The molecular mass of marker proteins (Rainbow™ from Amersham) is indicated in kDa at the right.

Figure 20:
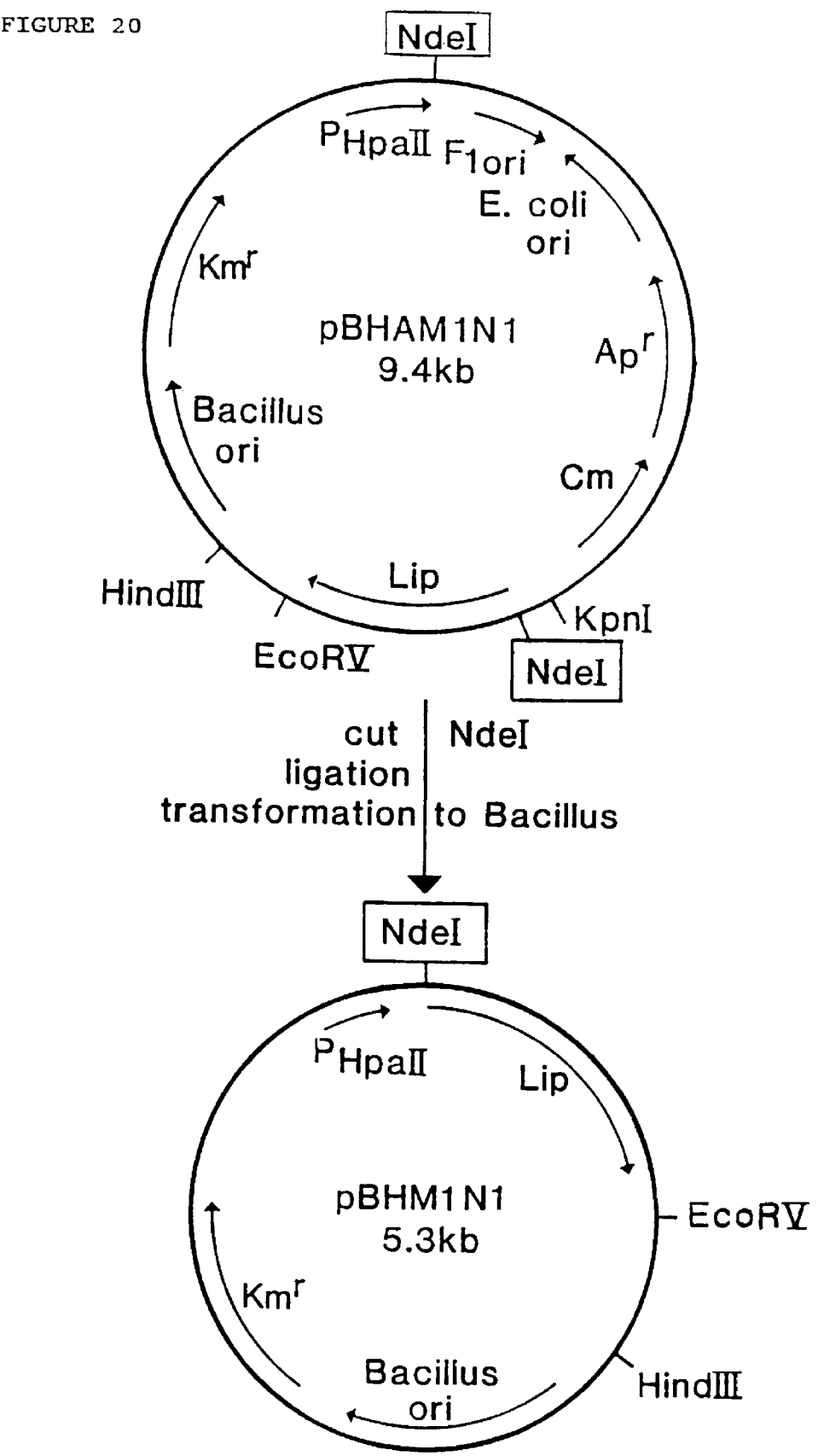

FIG. 20: The construction of plasmid pBHM1N1. The symbols are the same as used in FIG. 15.

FIG. 21: Autoradiograph of $^{35}$S labeled proteins synthesized in vitro.

Lanes A–D: Immunoprecipitation of the in vitro translated samples by monoclonal antibodies against M-1 lipase.

Lanes E–H: In vitro transcription/translation products of the following plasmids:

Lanes A and E: pTZ18RN
Lanes B and F: pTMPv18A
Lanes C and G: pMCTM1
Lanes D and H: pMCTbliM1

FIGS. 22A and 22B: Detection of lipase encoding sequences in bacterial DNAs. Five nanogram amounts of plasmid DNA and five microgram amounts of chromosomal DNA were digested with restriction enzyme as indicated, separated on 0.8% agarose gel blotted onto nitrocellulose filters and hybridized with the nick-translated insert of pET3 and pTMPv18A, respectively.

FIG. 22A shows the autoradiograph after hybridization with the pET3 EcoRI insert.

FIG. 22B shows the autoradiograph after hybridization with the pTMPv18A XhoI-EcoRV insert.

Lane A: HindIII/SStI digest of plasmid pTMPv18A
Lane B: EcoRI digest of plasmid pET3.
BRL DNA gel marker. MW of 0.5, 1.0, 1.6, 2.0, 3.0, 4.0, 5.0, 6.0, 7, 8, 9, 10, 11, 12 kb
Lane C: SalI digest of *P. pseudoalcaligenes* M-1 (CBS 473.85)
Lane D: SalI digest of *P. pseudoalcaligenes* IN II-5 (CBS 468.85)
Lane E: SalI digest of *P. alcaligenes* DSM 50342
Lane F: SalI digest of *P. aeruginosa* PAC 1R (CBS 136.89)
Lane G: SalI digest of *P. aeruginosa* PA02302 (6-1)
Lane H: SalI digest of *P. stutzeri* Thai IV 17-1 (CBS 461.85)
Lane I: SalI digest of *P. stutzeri* PG-I-3 (CBS 137.89)
Lane J: SalI digest of *P. stutzeri* PG-I-4 (CBS 138.89)
Lane K: SalI digest of *P. stutzeri* PG-II-11.1 (CBS 139.89)
Lane L: SalI digest of *P. stutzeri* PG-II-11.2 (CBS 140.89)
Lane M: SalI digest of *P. fragi* serm. DB1051 (=Ferm BP 1051)
Lane N: SalI digest of *P. gladioli* (CBS 176.86)
Lane O: SalI digest of *A. calcoaceticus* Gr-V-39 (CBS 460.85)
Lane P: SalI digest of *S. aureus* (ATCC 27661).

DESCRIPTION OF THE SPECIFIC EMBODIMENTS

In accordance with the subject invention, novel DNA constructs and novel compositions comprising microbial strains producing lipolytic enzymes are provided. The lipases of interest in the present invention possess a pH optimum between about 8 and 10.5, exhibit effective lipase activity in an aqueous solution containing a cleaning composition at concentrations of up to about 10 g/l under washing conditions at a temperature of 60° C. or below, preferably 30°–40° C., and at a pH between about 7 and 11, and preferably between about 9 and 10.5. Plasmid constructs comprising a DNA sequence encoding a lipase gene with the desired characteristics are used to transform a host cell which may be either a eukaryotic or prokaryotic cell. The transformed host cell is then grown to express the gene.

The techniques used in isolating the lipase gene are known in the art, including synthesis, isolation from genomic DNA, preparation from cDNA, or combinations thereof. The various techniques for manipulation of the gene are well known, and include restriction, digestion, resection, ligation, in vitro mutagenesis, primer repair, employing linkers and adaptors, and the like. See Maniatis et al., "Molecular Cloning", Cold Spring Harbor Laboratory, Cold Spring Harbor, N.Y., 1982.

Generally, the method comprises preparing a genomic library from an organism expressing a lipase with the desired characteristics. Examples of such lipases are those obtainable from Pseudomonas and Acinetobacter, and in particular from strains belonging to the species of *Pseudomonas alcaligenes, Pseudomonas pseudoalcaligenes, Pseudomonas aeruginosa, Pseudomonas stutzeri* and *Acinetobacter calcoaceticus*. A number of these lipases and strains are more fully described in EP-A-0218272, which disclosure is incorporated herein by reference. The genome of the donor microorganism is isolated and cleaved by an appropriate restriction enzyme, such as Sau3A. The fragments obtained are joined to a vector molecule which has previously been cleaved by a compatible restriction enzyme. An example of a suitable vector is plasmid pUN121 which can be cleaved by the restriction endonuclease BclI. Further, the amino acid sequence can be used to design a probe to screen a cDNA or a genomic library prepared from mRNA or DNA from cells of interest as donor cells for a lipase gene.

Furthermore, by using the lipase DNA or a fragment thereof as a hybridization probe, structurally related genes found in other microorganisms can be easily cloned. Particularly contemplated is the isolation of genes from organisms that express lipolytic activity using oligonucleotide probes based on the nucleotide sequence of lipase genes obtainable from the organisms described in EP-A-0218272. Alternatively, these oligonucleotides can be derived from the amino acid sequences of lipases of interest. Such probes can be considerably shorter than the entire sequence but should be at least 10, preferably at least 14, nucleotides in length. Longer oligonucleotides are also useful, up to the full length of the gene, preferably no more than 500, more preferably no more than 300, nucleotides in length. Both RNA and DNA probes can be used.

In use, the probes are typically labeled in a detectable manner (e.g., with $^{32}$p, $^{35}$S, $^{3}$H, biotin, or avidin) and are incubated with single-stranded DNA and RNA from the organism in which a gene is being sought. Hybridization is detected by means of the label after single-stranded and double-stranded (hybridized) DNA (DNA/RNA) have been separated (typically using nitrocellulose paper). Hybridization techniques suitable for use with oligonucleotides are well known to those skilled in the art.

Although probes are normally used with a detectable label that allows easy identification, unlabeled oligonucleotides are also useful, both as precursors of labeled probes and for use in methods that provide for direct detection of double-stranded DNA (or DNA/RNA).

Accordingly, the term "oligonucleotide probe" refers to both labeled and unlabeled forms.

In a preferred embodiment of this invention, the sequence from the *Pseudomonas pseudoalcaligenes* lipase is cloned from the strain CBS 473.85 (M-1). Surprisingly, the cloned lipase of *Pseudomonas aeruginosa* PAO (ATCC 15692), once sequenced showed a high degree of sequence homology with the lipase gene sequence of M-1. Even more surprisingly, a similar high degree of sequence homology was found between the lipase gene sequence of the M-1 strain and the chromosomal DNA of a number of *Pseudomonas stutzeri* isolates [viz. PG-I-3 (CBS 137.89), PG-I-4 (CBS 138.89, PG-II-11.1 (CBS 139.89), PG-II-11.2 (CBS 140.89)] and *Pseudomonas alcaligenes* DSM 50342. A "high degree of hybridization" as used in this specification is defined as a continuous sequence stretch of DNA of at least 300 bp wherein at least 67% homology is found.

The lipase enzymes of P. aeruginosa and P. stutzeri were produced and tested for their cleaning performance in the SLM-test. It was surprisingly found that all enzymes showing high levels of homolgy with the M-1 lipase gene, also showed superior stability, effectivity and performance under conditions simulating a modern washing process. According to Ausubel et al., Current Protocols in Molecular Biology, 1987–1988, the technique of Southern hybridization is capable of detecting homology to this level. The homologies found were not observed with the P. gladioli described in EP-A-0205208 and EP-A-0206390 or the Humicola languinosa lipase, described in EP-A-0305216.

Clones containing the inserted DNA fragment may be identified using a direct or positive selection procedure such as that developed for E. coli (Kuhn et al., Gene 44 (1986) 253–263) and for B. subtilis (Gryczan and Dubnau, Gene 20 (1982) 459–469). An example of such a positive selection vector for E. coli is pUN121 (Nilsson et al., Nucleic Acids Res. 11 (1983) 8019–8030).

In addition, clones expressing lipolytic enzymes may be identified, for example, using a suitable indicator plate assay, such as agar media containing tributyrin or olive oil in combination with rhodamine B (Kouker and Jaeger, Appl. Env. Microbiol. 53 (1987) 211). Further, replicated colonies may be screened using an adapted soft agar technique based on the procedure described for detecting esterase activity (Hilgerd and Spizizen, J. Bacteriol. 114 (1978) 1184). Alternatively, clones expressing lipolytic enzymes may be identified by using genetic complementation in a suitable lipase-negative recipient strain, such as described by Wohlfarth and Winkler, J. Gen. Microbiol. 134 (1988) 433–440.

Once a complete gene has been identified, either as cDNA or chromosomal DNA, it may then be manipulated in a variety of ways to provide for expression. Microbial hosts may be employed which may include, for example, bacteria, yeasts and fungi, such as E. coli, Kluyveromyces, Aspergillus, Bacillus and Pseudomonas species. Therefore, where the gene is to be expressed in a host which recognizes the wild-type transcriptional and translational regulatory regions of the lipase, the entire gene with its wild-type 5' and 3' regulatory regions may be introduced into an appropriate expression vector. Various expression vectors exist employing replication systems from prokaryotic cells. See, for example, Pouwels et al., "Cloning Vector, A Laboratory Manual", Elsevier, 1985. These replication systems have been developed to provide for markers which allow for selection of transformants, as well as providing for convenient restriction sites into which the gene may be inserted.

Where the gene is to be expressed in a host which does not recognize the naturally occurring wild-type transcriptional and translational regulatory regions, further manipulation will be required. Conveniently, a variety of 3'-transcriptional regulatory regions are known and may be inserted downstream from the stop codons. The non-coding 5'-region upstream from the structural gene may be removed by endonuclease restriction, Bal31 resection, or the like. Alternatively, where a convenient restriction site is present near the 5' terminus of the structural gene, the structural gene may be restricted and an adapter employed for linking the structural gene to a promoter region, where the adapter provides for lost nucleotides of the structural gene.

Various strategies may be employed for providing for an expression cassette, which in the 5'–3' direction of transcription has a transcriptional regulatory region and a translational initiation region, which may also include regulatory sequences allowing for the induction of regulation; an open reading frame encoding a lipolytic enzyme, desirably including a secretory leader sequence recognized by the proposed host cell; and translational and transcriptional termination regions. The expression cassette may additionally include at least one marker gene. The initiation and termination regions are functional in the host cell, and may be either homologous (derived from the original host), or heterologous (derived from the original host), or heterologous (derived from a foreign source or from synthetic DNA sequences). The expression cassette thus may be wholly or partially derived from natural sources, and either wholly or partially derived from sources homologous to the host cell, or heterologous to the host cell. The various DNA constructs (DNA sequences, vectors, plasmids, expression cassettes) of the invention are isolated and/or purified, or synthesizend and thus are not "naturally occurring".

Choice of appropriate regulatory sequences will take into account the following factors which affect expression. In terms of transcriptional regulation, the amount and stability of messenger RNA are important factors which influence the expression of gene products. The amount of mRNA is determined by the copy number of the particular gene, the relative efficiency of its promoter and the factors which regulate the promoter, such as enhancers or repressors. Stability of the mRNA is governed by the susceptibility of the mRNA to ribonuclease enzymes. In general, exonuclease digestion is inhibited by the presence of structural motifs at the ends of the mRNA; palindromic structures, altered nucleotides or specific nucleotide sequences. Endonuclease digestion is believed to occur at specific recognition sites within the mRNA and stable mRNAs would lack these sites. There is also some evidence that mRNAs undergoing high levels of translation are also protected from degradation by the presence of ribosomes on the mRNA.

In terms of translational regulation, given the presence of mRNA, expression can be regulated by influencing the rate of initiation (ribosome binding to the mRNA), the rate of elongation (translocation of the ribosome across the mRNA), the rate of post-translational modifications and the stability of the gene product. The rate of elongation is probably affected by codon usage, in that the use of codons for rare tRNAs may reduce the translation rate. Initiation is believed to occur in the region just upstream of the beginning of the coding sequence. In prokaryotes, in most cases this region contains a consensus nucleotide sequence of AGGA, termed the Shine-Dalgarno sequence. While this sequence characterizes the ribosomal binding site, it is evident that sequences both upstream and downstream can influence successful initiation.

Evidence also points to the presence of nucleotide sequences within the coding region which can affect ribosome binding, possibly by the formation of structural motifs through which the ribosome recognizes the initiation site. Position of the AGGA sequence with respect to the initiating ATG codon can influence expression. It is thus the interaction of all of these factors which determines a particular expression rate. However, the expressed genes have evolved a combination of all of these factors to yield a particular rate of expression. Design of an expression system to yield high levels of gene product must take into consideration not only the particular regions that have been determined to influence expression but also how these regions (and thus their sequences) influence each other.

Illustrative transcriptional regulatory regions or promoters include, for example, those sequences derived from genes overexpressed in industrial production strains.

The transcriptional regulatory region may additionally include regulatory sequences which allow expression of the structural gene to be modulated, for example by presence or absence of nutrients or expression products in the growth medium, temperature, etc. For example, in prokaryotic cells expression of the structural gene may be regulated by temperature using a regulatory sequence comprising the bacteriophage lambda $P_L$ promoter together with the bacteriophage lambda $O_L$ operator and a temperature-sensitive repressor. Regulation of the promoter is achieved through interaction between the repressor and the operator. Of particular interest are expression cassettes capable of expressing a lipolytic enzyme which employ the regulatory sequences of Bacillus amylase and protease genes. The structural gene of interest is joined downstream from the ribosomal binding site, so as to be under the regulatory control of the transcriptional regulatory region and the translational initiation region.

In addition, a fused gene may be prepared by providing a 5'-sequence to the structural gene which encodes a secretory leader and a processing signal. If functional in the host cell of choice, the signal sequence of the lipase gene itself may also be employed. Illustrative heterologous secretory leaders include the secretory leaders of penicillinase, amylase, protease and yeast alpha-factor. By fusion in proper reading frame with a secretory leader with the structural gene of interest, the mature lipolytic enzyme may be secreted into the culture medium.

The expression cassette may be included within a replication system for episomal maintenance in an appropriate host microorganism or may be provided without a replication system, where it may become integrated into the host genome. The manner of transformation of the host microorganism with the various DNA constructs is not critical to this invention. The DNA may be introduced into the host in accordance with known techniques, such as transformation, using calcium phosphate-precipitated DNA, conjugation, electroporation, transfection by contacting the cells with a virus, micro-injection of the DNA into cells, or the like. The host cells may be whole cells or protoplasts.

As a host organism, any microorganism may be used which is suitable for production and extraction of a lipolytic enzyme; preferably the host organism is also capable of secreting the enzyme produced whereby the enzyme can be recovered from the cell-free fermentation fluid. The host microoganism is also preferably a non-pathogenic organism. Examples of host organisms which fulfill the above criteria include *E. coli, Pseudomonas putida* and Bacillus strains, especially *B. subtilis* and *B. licheniformis,* Streptomyces strains and fungi and yeast strains such as Aspergillus and Kluyveromyces, respectively.

The host strains may be laboratory strains, or can include industrial strain microorganisms. Industrial strains are characterized as being resistant to genetic exchange, such as phage infection or transformation. The strains are stable and may or may not be capable of spore formation. They are prototrophic and modified to provide for high yields of endogenous protein products, such as the enzymes alpha-amylase and various proteases. The yield of an endogenous protein product obtained in an industrial production process can amount to at least 5 g/l (0.5% w/v). Industrial strains also secrete DNases, which result in the degradation of DNA in the medium, providing for protection against genetic exchange.

Once the structural gene has been introduced into the appropriate host, the host cell may be grown to express the structural gene. Production levels of lipolytic activity may be comparable to or higher than the original strains from which the genes are derived. The host cell may be grown to high density in an appropriate medium to form a nutrient-rich broth. Where the promoter is inducible, permissive conditions will then be employed, for example, temperature change, exhaustion, or excess of a metabolic product or nutrient, or the like.

Where secretion is provided for, the expression product may be isolated from the growth medium by conventional means. Release of the produced lipolytic enzyme may be enhanced by dilute surfactant solutions. Where secretion is not provided for, host cells may be harvested and lysed in accordance with conventional conditions. The desired product is then isolated and purified in accordance with known techniques, such as chromatography, electrophoresis, solvent extraction, phase separation, or the like.

The subject compositions can be used in a wide variety of ways. The transformed host microorganisms can be used for enhanced production of lipase having characteristics which make it useful in detergent compositions. The cloned lipase genes may also find use in screening for lipase genes, including identification of a lipolytic gene as a lipase rather than an esterase.

They may also be used for enzyme engineering using known techniques relating to random or site-directed mutagenesis resulting in lipases with the required altered characteristics.

The lipolytic enzyme compositions can be used in washing compositions together with a detergent and optionally other ingredients which are commonly used in cleaning compositions. These ingredients can include at least one of surfactants, water softeners such as complex phosphates, alkali metal silicates and bicarbonates; fillers such as alkali metal sulfate; other emzymes such as proteases and amylases; bleaching agents; as well as miscellaneous compounds such as perfumes, optical brighteners, etc.

In the enzymatic cleaning composition according to the invention, the lipase activity is preferably in the range of from 1 to 20,000 TLU/g of composition, while the proteolytic enzyme activity is preferably in the range of from 50 to 10,000 Delft Units/g of cleaning composition. One TLU (true lipase unit) is defined as the titratable fatty acids equivalent to the amount of 1 $\mu$mole NaOH/min released from olive oil/Arabic gum emulsion at pH 8.0, 25° C. The Delft Units are defined in J. Amer. Oil Chem. Soc. 60 (1983) 1672.

The cleaning compositions of the invention may be prepared in the usual manner, for example by mixing together the components or by the preparation of an initial premix, which is subsequently finished by mixing with the other ingredients. According to one possible preparation route, one or more lipase preparations are mixed with one or more of the other compounds to make a concentrate of a predetermined enzymatic activity, which concentrate can then be mixed with the other desired components.

Preferably, the lipolytic enzymes of the invention are in the form of an enzymatic detergent additive. This additive may also contain one or more other enzymes, for example a protease and/or an amylase, which can be used in modern washing compositions, and one or more other components, which are commonly used in the art, for example a non-ionic, salt, stabilizing agent and/or coating agent. The enzymatic detergent additive can comprise in addition to a lipase, a protease and optionally an alpha-amylase. The proteolytic enzymes are compatible with the lipolytic enzymes in this formulation. The enzymatic detergent additives are generally mixed with one or more detergents and other components known in the art to form washing compositions. The enzymatic detergent additive, is generally used, in the range from $10^2$ and $10^7$ TLU/g of additive, while the optionally present proteolytic activity is in the range of from $5 \times 10^4$ to $10^6$ Delft Units/g.

The enzymatic detergent additives of the invention may be in the form of, for example, granulates or prills, prepared according to methods which are generally known in the art. See, for example, British Patents Nos. 1,324,116 and 1,362,365 and U.S. Pat. Nos. 3,519,570, 4,106,991 and 4,242,219.

The enzymatic detergent additive can be in liquid form with an enzyme stabilizer, for example propylene glycol. They can also be in the form of organic or inorganic slurries, emulsions or encapsulates, immobilized on a soluble or insoluble support or in an aqueous or water-free solution in the presence of one or more stabilizers. Such additives are preferably used in liquid detergent compositions.

The following examples are offered by way of illustration and not by way of limitation.

EXPERIMENTAL

General cloning techniques were used as described by Maniatis et al., "Molecular Cloning: A Laboratory Manual", Cold Spring Harbor Laboratory, 1982, CSH, New York. All DNA-modifying enzymes were obtained from commercial suppliers. They were used according to the manufacturer's instructions. Materials and apparatus for DNA purification and separation were used according to the instructions from the supplier.

EXAMPLE 1

Molecular Cloning of Triacylglycerol Acylhydrolases

A. Source of DNA and Selection Vector

EP-A-0218272 discloses several strains of bacteria which produce lipases suitable for use in detergents. Of these, *Acinetobacter calcoaceticus* Gr V-39 (CBS 460.85), *Pseudomonas stutzeri* Thai IV 17-1 (CBS 461.85), *Pseudomonas pseudoalcaligenes* IN II-5 (CBS 468.85) and *Pseudomonas pseudoalcaligenes* M-1 (CBS 473.85) were selected as a source of lipolytic genes.

Plasmid vector pUN121 (Nilsson et al., Nucleic Acids Research 11 (1983) 8019) which carries an ampicillin resistance gene, a tetracycline resistance gene and the cI repressor gene of bacteriophage lambda was obtained from Dr. M. Uhlen, Royal Institute of Technology, Department of Biochemistry, Teknikringen 10, S-10044 Stockholm, Sweden. Transcription of the tetracycline gene is prevented by the cI repressor. Insertion of foreign DNA into the unique restriction sites (BclI, SmaI, HindIII and EcoRI) results in activation of the tetracycline gene. This permits direct (positive) selection of recombinant transformants on Luria broth agar plates containing 8 μg/ml tetracycline and 50 μg/ml ampicillin.

Figure 1:
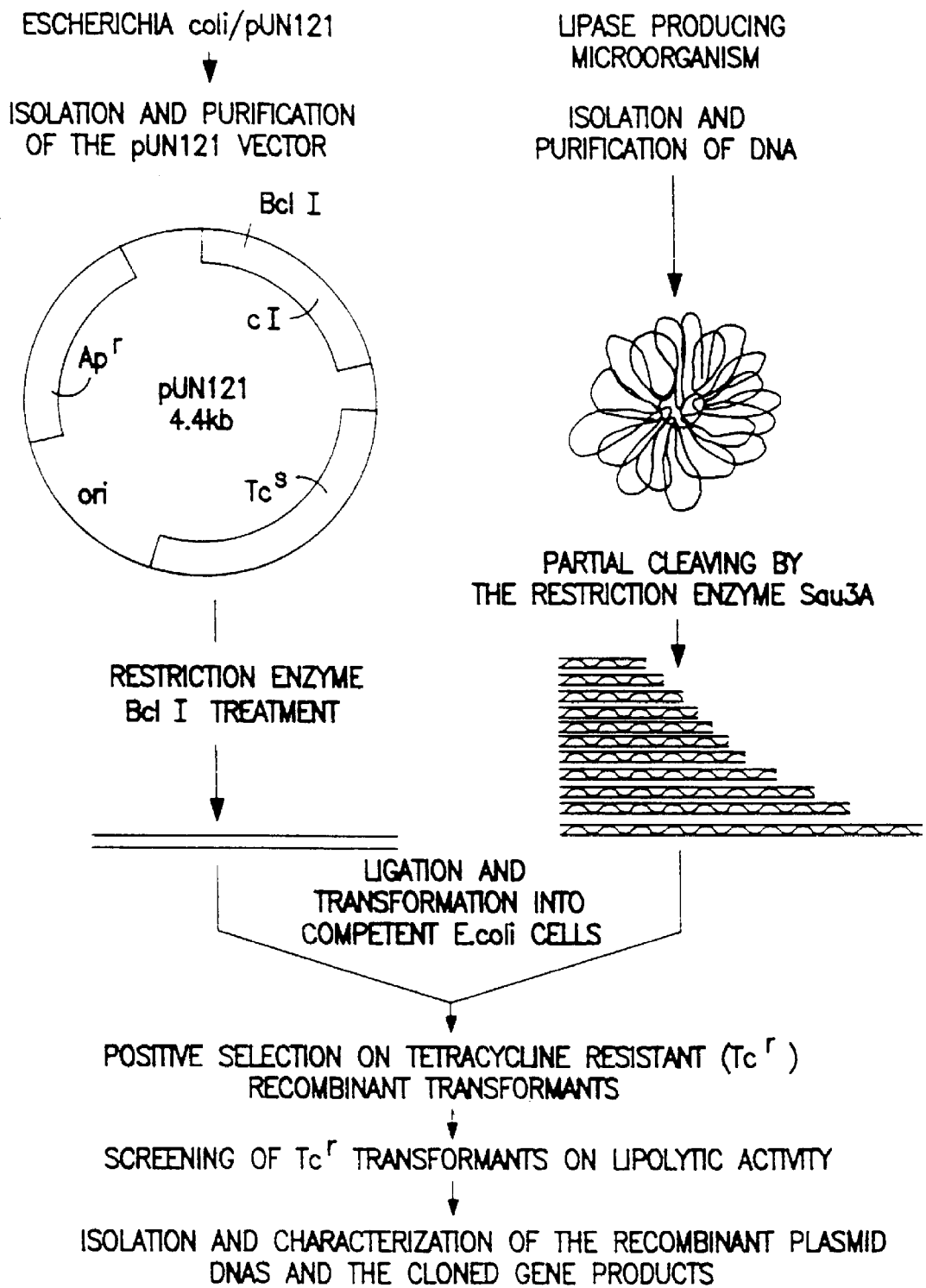
FIG. 1: Strategy of the lipolytic enzyme gene cloning. For symbols see the legend in FIG. 2.

B. Preparation of Gene Library (see FIG. 1)

Plasmid and chromosomal DNA was isolated as described by Andreoli, Mol. Gen. Genet. 199 (1985) 372–380. Chromosomal DNA isolated from Thai IV 17-1 and M-1, respectively, was partially Sau3A digested. The DNA was then ligated with T4 DNA ligase to BclI digested pUN121 DNA as described by Maniatis et al. (supra) and transformed into competent cells of *E. coli* strain JM101 hsdS recA (Dagert and Ehrlich, Gene 6 (1979) 23–28). *E. coli* JM101 hsdS recA was obtained from the Phabagen Collection (Accession Number PC2495), Utrecht, The Netherlands. Transformants resistant to tetracycline at 8 μg/ml in Luria broth agar plates were selected for.

C. Screening for Transformants

The gene library obtained as described above was replica-plated and screened for lipolytic activity using the following two procedures. In the first procedure, the replicated colonies were screened for lipolytic activity on peptone agar media containing tributyrin. Lipolytic activity was detected as a zone of clearing (halo) around a colony due to the degradation of the turbid lipid emulsion. In the second procedure, replicated colonies were screened for esterase activity using a soft agar overlay technique. The method was based on that of Hilgerd and Spizizen, J. Bacteriol. 114 (1987) 1184. Essentially a mixture of 0.4% low-melting agarose, 0.5M potassium phosphate (pH 7.5), 0.5 mg/l β-naphthyl acetate, dissolved in acetone, and 0.5 mg/l Fast Blue BB (see Example 2) was poured over the transformants. Within a few minutes colonies with esterase or lipase activity coloured purple.

Of the 1200 tetracycline resistant transformants obtained from the Thai IV 17-1/pUN121 gene bank, three produced halos on tributyrin agar plates. Of the 12,000 recombinant transformants tested from the M-1/pUN121 gene bank, only one clone tested showed weak lipolytic activity.

The tributyrin-positive clones were grown overnight in 2TY medium (16 g/l Bacto-tryptone, 10 g/l Bacto-yeast extract, 5 g/l NaCl, pH 7.0) medium and assayed for both the plasmid content (see under 1D) and the ability to convert various β-naphthyl substrates, an indication of lipolytic activity (see Example 2A).

D. Plasmid Isolation

D.1 Containing Thai IV 17-1 Lipase Gene

The plasmids isolated from the Thai IV 17-1/pUN121 transformants were designated pAT1 and pAT3. Their structures are presented in FIGS. 2 and 3, respectively. A third clone, designated pAT2, harboured a plasmid identical to the pAT1 construct. The gene encoding the lipolytic activity was located within a 2.7 kb EcoRI fragment of pAT1 (FIG. 2, dashed line) and within a 3.2 kb EcoRI fragment of pAT3 (FIG. 3, dashed line). The two EcoRI fragments were subcloned in appropriate vectors, both for DNA sequencing and for obtaining higher yields of lipolytic activity.

Cloning of the 2.7 kb EcoRI fragment from pAT1 in the pUN121 vector generated the recombinant plasmid pET1 (FIG. 4). A sample of *E. coli* JM101 hsdS recA harbouring plasmid pET1 was deposited with CBS on Feb. 5, 1987, under No. CBS 157.87.

Cloning of the 3.2 kb EcoRI fragment from pAT3 in the pUN121 vector generated the recombinant plasmid pET3 (FIG. 5). A sample of *E. coli* JM101 hsdS recA harbouring plasmid pET3 was deposited with CBS on Feb. 5, 1987, under No. CBS 155.87.

D.2 Containing M-1 Lipase Gene

The recombinant plasmid isolated from the M-1/ pUN121 transformant named pAM1 was isolated and characterized (FIG. 6). Biochemical characterization of the lipolytic activity of pAM1, however, showed that this plasmid did not encode the lipase aimed for (see also Examples 2 and 3). Therefore, other strategies had to be developed which are illustrated hereinafter.

The plasmid pAM1 in *E. coli* JM101 hsdS recA was deposited with CBS on Feb. 5, 1987, under No. 154.87.

D.3 Containing IN II-5 Lipase Gene

Partially Sau3A digested *Pseudomonas pseudoalcaligenes* IN II-5 DNA fragments were cloned in *E. coli* K12 DH1 strain (ATCC 33849) using plasmid vector pUN121.

After ligation and transformation to competent DH1 cells prepared as described by Hanahan, J. Mol. Biol. 166 (1983) 557–580, about 1500 transformants resistant to 50 μg/ml ampicillin and 8 μg/ml tetracycline were obtained. Transformants capable of hydrolyzing tributyrin and β-naphthyl acetate were selected for as described under 1C. From one positive colony, plasmid DNA was isolated and characterized by determining several restriction enzyme recognition positions. The physical map of this plasmid, named pM6-5, is shown in FIG. 7.

The activity of *E. coli* DH1 (pM6-5) towards β-naphthyl esters was determined (Table 1). A sample of *E. coli* DH1 harbouring plasmid pM6-5 was deposited with CBS on Feb. 5, 1987, under No. 153.87.

D.4 Containing Gr V-39 Lipase Gene

Partially EcoRI* digested (conditions according to Gardner et al., DNA 1 (1982) 109–114) *Acinetobacter calcoaceticus* Gr V-39 DNA was mixed with EcoRI linearized pUN121 DNA. After recircularization by the use of $T_4$ polynucleotide ligase, the DNA mixture was introduced into *E. coli* DH1 (ATCC 33849) using the transformation procedure described earlier in this Example. All 1800 tetracycline-resistant transformants obtained were screened for lipolytic activity as described under 1C.

Three clones of this Gr V-39/pUN121 gene library produced a lipolytic enzyme. Plasmid DNA from one of these clones, named pP5-4, was isolated and characterized with restriction endonucleases. The physical map of this plasmid pP5-4 is shown in FIG. 8. The hydrolysis of β-naphthyl esters by crude enzyme preparations from *E. coli* DH1 (pP5-4) was then determined (Table 1). Plasmid pP5-4 in *E. coli* DH1 was deposited with CBS on Feb. 5, 1987, under No. 151.87.

EXAMPLE 2

Characterization of Cloned Lipolytic Enzyme Preparations

A. Determination of Lipolytic Activity

Tributyrin-positive *E. coli* colonies were inoculated in 100 ml 2TY medium containing ampicillin and tetracycline in a 500 ml conical flask. *E. coli* cultures were shaken for 40 hrs at 30° C. in an orbital shaker at 250 rpm. The Pseudomonas and Acinetobacter strains were grown at 30° C. After 40 hrs the optical density at 575 nm was measured and the broth was centrifuged in a Sorvall RC5B centrifuge in a GSA rotor at 6,000 rpm for 10 min. The supernatant was stored at 4° C. until enzyme assay.

The cells were resuspended in 4 ml lysis buffer (25% sucrose, 50 mM Tris-HCl pH 7.5). Lysozyme was added and after 30 min of incubation at 21° C. DNase (20 μg/ml) was added and the incubation continued for 30 min at 37° C. Triton-X100 (0.1% v/v) was added and the cell suspensions sonicated on ice with a Labsonic 1510 sonifier set (5 strokes for 30 sec at 100 Watts with 1 min intervals). The cell debris was then removed by centrifugation for 15 min. at 12,000 rpm in a Hettich Mikro Rapid/K centrifuge. The supernatant obtained was then assayed for lipolytic activity. The assay is based on the hydrolysis of β-naphthylesters by lipolytic enzymes. The β-naphthyl released reacts with the diazonium salt Fast Blue BB to produce an azo dye absorbing at 540 nm. The method is essentially that of McKellar, J. Dairy Res. 53 (1986) 117–127, and was performed as follows.

The reaction tube contained in a final volume of 2.0 ml: 1.8 ml 55 mM TES (N-tris(hydroxy-methyl)methyl-2-aminoethane sulphonic acid, Sigma); 0.02 ml 100 mM β-naphthyl ester dissolved in dimethyl sulphoxide (DMSO, Merck) or Methyl-cellusolve® acetate (Merck), 0.1 ml 120 mM NaTC (Na-taurocholate, Sigma), and 0.1 ml of an enzyme preparation.

Controls lacking enzyme and β-naphthyl (Sigma) standards lacking enzyme and substrate were also used.

Corning centrifuge tubes (15 ml) containing the reaction mixture were incubated at 37° C. or specified temperature for 30 min. A 0.02 ml 100 mM FB solution (Fast Blue BB salt (Sigma), dissolved in DMSO) was added and the incubation continued for 10 min. The reaction was terminated with 0.2 ml 0.72N TCA (trichloroacetic acid, Riedel-De Haen) and the coloured complex was extracted by vigorous mixing with 2.5 ml 1-butanol (Merck). The layers were separated by centrifugation at 5,000 rpm for 5 min. in a Heraeus Christ minifuge RF. The absorbance of the top layer was measured at 540 nm using a LKB ultraspec II spectrophotometer. After subtraction of controls, the readings were converted to TLUs (True Lipase Units) using *Candida cylindracea* lipase (L1754, Sigma) as a standard. One TLU is defined as the titratable fatty acids equivalent to the amount of 1 μmole NaOH/min (see also EP-A-0218272). The results are shown in Table 1 below.

Comparison of the hydrolysis data of the β-naphthyl esters, varying in acyl chain length from $C_4$ to $C_{18}$, indicate that: 1°. the clones harbouring the pAT3 and pET3 plasmids produce true lipases; and 2°. the clones harbouring the pAT1, pET1, pAM1, pP5-4 and pM6-5 plasmids produce enzymes with substantial esterase activities. Most of the lipolytic enzymes synthesized by *E. coli* carrying recombinant plasmids were found in the cell lysates.

TABLE 1

Colorimetric Determination of Lipolytic Acitivity (in TLU · $l^{-1}$) in Samples from Donor Microorganisms and *E. coli* Transformants

| | | β-naphthyl Substrate | | | | | | | |
|---|---|---|---|---|---|---|---|---|---|
| | | β-NB(4) | | β-NC(8) | | β-NL(12) | | β-NO(18) | |
| Host Strain | Plasmid | sup | lysate | sup | lysate | sup | lysate | sup | lysate |
| *E. Coli* K12 | | | | | | | | | |
| JM101 hsdS recA | pAT1 | 22 | 80 | 4 | 66 | 1 | 20 | 1 | 10 |
| JM101 hsdS recA | pET1 | 2 | 66 | 4 | 88 | 1 | 25 | 1 | 8 |
| JM101 hsdS recA | pAT3 | 24 | 80 | 4 | 132 | 4 | 42 | 2 | 60 |
| JM101 hsdS recA | pET3 | 5 | 90 | 4 | 22 | 1 | 12 | 1 | 54 |
| JM101 hsdS recA | pAM1 | 1 | 4 | 4 | 8 | 1 | 4 | 1 | 1 |
| JM101 hsdS recA | pUN121 | 1 | 1 | 2 | 4 | 1 | 2 | 1 | 1 |

TABLE 1-continued

Colorimetric Determination of Lipolytic Acitivity (in TLU · $1^{-1}$)
in Samples from Donor Microorganisms and *E. coli* Transformants

| | | β-naphthyl Substrate | | | | | | | |
|---|---|---|---|---|---|---|---|---|---|
| | | β-NB(4) | | β-NC(8) | | β-NL(12) | | β-NO(18) | |
| Host Strain | Plasmid | sup | lysate | sup | lysate | sup | lysate | sup | lysate |
| (control) | (vector) | | | | | | | | |
| DH1 | pP5-4 | 1 | 2 | 4 | 6 | 1 | 4 | 1 | 6 |
| DH1 | pM6-5 | 1 | 2 | 4 | 7 | 1 | 15 | 1 | 7 |
| DH1 (control) | pUN121 (vector) | 1 | 1 | 2 | 4 | 1 | 2 | 1 | 1 |
| Pseudomonas | | | | | | | | | |
| M-1 | N.D. | 5 | 8 | 23 | 40 | 14 | 34 | 11 | 20 |
| IN II-5 | N.D. | 50 | 52 | 58 | 66 | 17 | 37 | 7 | 22 |
| THAI IV 17-1 | N.D. | 23 | 28 | 10 | 60 | 9 | 40 | 31 | 25 |
| Acinetobacter | | | | | | | | | |
| GR V-39 | N.D. | 6 | 10 | 17 | 21 | 15 | 20 | 5 | 12 |

N.D. = Not Determined

B. Further Characterization of Cloned Lipolytic Preparations

The cloned lipolytic enzyme preparations were characterized using SDS gel electrophoresis on a Phastgel system (Pharmacia) using a Phastgel gradient 10–15% according to the manufacturer's instructions. Cell-free extracts from the *E. coli* clones pET3 and the DH1 strain with the pUN121 vector were compared with partially purified enzyme from the donor strain Thai IV 17-1 (Stuer et al., J. Bacteriol. 168 (1986) 1070–1079).

Sample preparation. Four volumes of an appropriate dilution of the enzyme preparations were mixed with one part of sample buffer containing 10% SDS, 10% β-mercaptoethanol in 0.5M Tris-HCl, pH 6.8. This solution was divided into three equal parts. One portion received no further treatment but was kept at room temperature until gel electrophoresis took place. The second and third portions were heated for 5 and 10 min at 95° C., respectively, followed by cooling down in ice, then kept at room temperature until subjected to gel electrophoresis.

Electrophoresis. The treated samples, in duplicate, were electrophoresed on the Phastgel system at 65 Volts/hour. One gel was stained for protein with Coomassie Brillant Blue according to Pharmacia Development technique file no 200. FIG. 9A shows the polypeptide patterns after staining with Coomassie Brillant Blue. The second gel was washed with 50 mM Tris-HCl pH 7.5, 0.1% Triton X-100 to remove SDS and to reactivate the enzyme activity. The presence of lipolytic activity in the washed gel was visualized by a soft agar overlay technique based on the β-naphthyl acetate/Fast Blue BB salt method described in Example 1C. After incubation for 30 min at 30° C., purple bands became visible against a clear background. As shown in FIG. 9B, the lipase from the *E. coli* pET3 clone and native *P. stutzeri* Thai IV 17-1 lipase (MW 40 kDa) had identical mobilities on SDS gel-electrophoresis. Both enzymes show a so-called heat modifiability. A similar heat modifiability was described for the outer membrane protein (OmpA gene product) of *E. coli* K12, Freudl et al., J. Biol. Chem. 261 (1986) 11355–11361.

EXAMPLE 3

Construction of a *Pseudomonas pseudoalcaligenes* Gene Library in Broad Host Range Vectors As an alternative strategy for the cloning of the lipase gene from the *P. pseudoalcaligenes* M-1 strain, a binary broad host range cloning system was used, which enabled the gene bank to be screened directly by complementation against various mutant strains of Pseudomonaceae. Two broad host range vectors pLAFR1 (Friedman et al., Gene 18 (1982) 289–296) and pKT248 (Bagdasarian et al., Gene 16 (1981) 237–247) were used. Plasmid pLAFR1 is a RK2-derived broad host-range cosmid conferring tetracycline resistance and is mobilizable but not self-transmissable. Plasmid pKT248 is a mobilizable R300B-derived broad host range plasmid conferring streptomycin and chloramphenicol resistance. Mobilization of these vectors from *E. coli* to Pseudomonas was performed with the aid of the plasmid pRK2013, which contains RK2 transfer functions (Ditta et al., Proc. Natl. Acad. Sci. U.S.A. 77 (1980) 7347–7351) according to the triparental mating procedure of Friedman et al., (Gene 18 (1982) 289–296). A lipase-negative mutant 6-1 of *P. aeruginosa* strain PAO 2302 (obtained from S. Wohlfarth and U. K. Winkler, Ruhr Universität, Bochum, FRG) was used as Pseudomonas recipient (J. Gen. Microbiol. 134 (1988) 433–440).

The preparation of in vitro lambda phage packaging extracts and the packaging of pLAFR1 DNA were performed essentially as described by Ish-Horowicz and Burke (Nucleic Acids Res. 9 (1981) 2989–2998). Briefly, total *P. pseudoalcaligenes* M-1 DNA was partially cleaved with EcoRI or SalI and was ligated to either EcoRI restricted pLAFR1 DNA or SalI restricted pKT248 DNA. The ratio of insert to vector was 5:1 to reduce the possibility of vector-to-vector ligation. The ligated M-1/pLAFR1 DNA was packaged in vitro into lambda phage heads and injected into *E. coli* DH1 (Maniatis et al., supra 1982).

Approximately 2,500 tetracycline resistant transductants were obtained per μg of *P. pseudoalcaligenes* M-1. Assuming that *P. pseudoalcaligenes* has a genome size of 5,000 kb and that at least 50% of the tetracycline-resistant transductants carry an insert of 20 kb, 2,300 independent clones were needed to assure a 99% probability of finding a particular DNA sequence (Clark and Carbon, Cell 9 (1976) 91). Since the gene library contained more than 8,000 different recombinant colonies it was likely to contain the entire *P. pseudoalcaligenes* genome.

The ligated M-1/pKT248 DNA was transformed into competent *E. coli* cells as described in Example 1. Transformants of *E. coli* JM101 hsdS recA were selected for streptomycin resistance (Sm$^R$) and contra-selected for chloramphenicol sensitivity (Cm$^S$). Five thousand Sm$^R$ Cm$^S$ clones were obtained. The two M-1 gene libraries obtained in the *E. coli* host were replica-plated and screened for lipolytic activity as described in Example 1. None of the 13,000 recombinant transformants examined showed a lipase activity.

Mobilization of the clone from *E. coli* to *P. aeruginosa* PAO 2302 (6-1) was therefore performed as follows. Recombinant plasmids were transferred to Pseudomonas recipients by replica-plating of donor strains to a lawn of the recipient strain (PAO2302/6-1) and helper strain (*E. coli* MC1061 or DH1 harbouring the pRK2013 plasmid). After overnight growth of donor, recipient and helper strain on a Heart Infusion agar plate, exconjugants were selected by replica-plating on minimal agar medium containing 0.2% citrate, methionine (10 μg/ml) and streptomycin or tetracycline.

Citrate is not metabolized by *E. coli*. Restoration of the lip phenotype of the lipase-defective mutant 6-1 with recombinant plasmids was tested by replica-plating the *P. aeruginosa* exconjugants on nutrient broth agar plates containing trioleoylglycerol and the fluorescent dye rhodamine B as described by Kouker and Jaeger, Appl. Env. Microbiol. 53 (1987) 211–213.

Four of the 13,000 screened exconjugants showed lipase activity as evidenced by the development of orange fluorescence halos, visible at 360 nm, around the bacterial colonies after 40 hrs of incubation at 37° C. One of these positive clones, pALM5, was chosen for further characterization.

Finally, to ascertain that the lipase produced by the PAO 2302/6-1 exconjugant harbouring pALM5 has the desired characteristics displayed by the lipase from *P. pseudoalcaligenes* M-1 strain, enzyme samples were prepared and subjected to both biochemical analysis (see Example 2) and the SLM test (as described hereinafter in Example 10). The results obtained in these tests indicated that the lipolytic activity of the enzyme produced by the pALM5 clone has similar characteristics to that of the enzyme obtained from the parent M-1 strain.

EXAMPLE 4

Molecular Cloning of the *Pseudomonas pseudoalcaligenes* M-1 Lipase Gene

A. Protein Purification and Sequence

The fermentation and preparation of a freeze-dried supernatant of the *Pseudomonas pseudoalcaligenes* M-1 strain are described in EP-A-0218272. The lipolytic enzyme was purified from this supernatant essentially according to Wingerder et al., Appl. Microbiol. Biotechnol. 27 (1987) 139–145. After purification the protein preparation was more than 80% pure as assessed by SDS-polyacrylamide gel-electrophoresis followed by staining with Coomassie Brilliant Blue (see FIG. 10).

N-terminal sequence analysis was performed after SDS gel-electrophoresis and electro-blotting on Immobilon transfer membrane (Millipore) according to Matsudaira (J. Biol. Chem. 262 (1987) 10035–10038). This analysis yielded the following sequence (using the conventional single letter amino acid code):

```
G L F G S T G Y T K T K Y P I V L T H G M L G F
1              10                  20
```

B. Cloning the M-1 Lipase Gene

Two synthetic 32-mer oligonucleotides:

5'ACC GGC TAC ACC AAG ACC AAG TAC CCC ATC GT-3' and

5'ACC GGC TAC ACC AAG ACC AAG TAC CCG ATC GT-3' were deduced from amino acids 6 to 15 (T G Y T K T K Y P I) of the N-terminal sequence of the mature lipase protein as described above, after taking into consideration the codon bias for Pseudomonaceae and the degeneracy of the genetic code. For use as a hybridization probe, the oligonucleotides were end-labeled using T4 polynucleotide kinase.

Chromosomal DNA was isolated from *Pseudomonas pseudoalcaligenes* M-1 strain (CBS 473.85) according to Andreoli (Mol. Gen. Genet. 199 (1985) 372–380), digested with several restriction endonucleases, and separated on an 0.8% agarose gel. Southern blots of these gels, using radiolabeled 32-mer oligonucleotide as a probe revealed the following unique hybridizing DNA bands: 1.8 kb BclI, 2.0 kb PvuII and 1.7 kb SalI. Therefore M-1 chromosomal DNA was digested separately with these three restriction endonucleases, fractionated by 0.8% agarose gel-electrophoresis and the hybridizing fractions as described above recovered by electro-elution in a bio-trap BT 1000 apparatus from Schleicher and Schull.

The 1.8 kb BclI digested fraction was ligated into BamHI-cut dephosphorylated vector pTZ18R/19R (purchased from Pharmacia, Woerden, The Netherlands). The 2.0 kb PvuII digested fraction was ligated into SmaI-cut dephosphorylated vector pTZ18R/19R. The 1.7 kb SalI digested fraction was ligated into SalI-cut dephosphorylated vector pZT18R/19R. All three ligations were transformed into competent *E. coli* JM101 hsdS recA cells (as described by Andreoli, supra) and plated on Luria broth agar plates which contained ampicillin, X-gal (5-bromo-4-chloro-3-indolyl-β-D-galactopyrano-side) and IPTG (isopropyl-β-D-thiogalactoside).

Approximately 4×10$^3$ white colonies were picked onto fresh agar plates and screened by colony hybridization to the radiolabeled 32-mer probe. Using this method 12 positive colonies were obtained. From each of these positive colonies a plasmid mini-prep was prepared by the alkaline lysis method and digested with the appropriate restriction endonucleases according to the instructions of the supplier. Six plasmids contained the expected hybridizing inserts. One of the plasmids which contained only the 2.0 kb PvuII fragment, designated as pTMPv18A, was selected for detailed analysis. A sample of *E. coli* JM101 hsdS recA harbouring plasmid pTMPv18A was deposited with CBS on Mar. 8, 1989, under No. CBS 142.89.

The *E. coli* pTZ18R/19R recombinant transformants obtained as described above were replica-plated and screened for lipolytic activity as described in Example 2. None of the 5×10$^4$ *E. coli* transformants examined showed lipolytic activity. Several reasons for this failure can be mentioned: a) the gene expression intiation signals of the M-1 lipase genes were either not recognized by the *E. coli* transcription/translation system (see, for example, Jeenes et al., Mol. Gen. Genet. 203 (1986) 421–429), b) a regulatory sequence or protein is necessary to switch on this M-1 lipase gene, c) proper folding or secretion of M-1 lipase in *E. coli* may be inadequate.

C. Characterization and Sequencing of the M-1 Lipase Gene

Plasmid pTMPv18A was digested with a variety of restriction enzymes which have 6 bp recognition sequences. Analysis of the fragment sizes resulting from these experiments allowed the generation of a preliminary restriction endonuclease cleavage map of the 2.0 kb PvuII insert of pTMPv18A. This map is shown in FIG. 11.

The pTZ18R/19R vectors used provide a versatile "all-in-one system" to permit DNA cloning, dideoxy DNA sequencing, in vitro mutagenesis and in vitro transcription (Mead et al., Protein Engineering 1 (1986) 67–74). The double-stranded plasmids were converted into single-stranded DNA by superinfection with a helper phage M13K07 obtained from Pharmacia.

A DNA sequence analysis of a 0.94 kb DNA fragment between the XhoI and the EcoRV of pTMPv18A is shown in FIG. 12. This DNA sequence when translated in all possible reading frames, revealed a large open reading frame which includes the $NH_2$-terminal amino acid residues of the lipase protein as determined by direct amino acid sequencing (residue 1–24), see this Example under A. The methionine at position −24 is the initiation codon of a preprotein because this methionine precedes a stretch of amino acids typical for bacterial signal peptides (see Von Heijne, J. Mol. Biol. 192 (1986) 287–290). This signal peptide of 24 amino acids is cleaved off during the secretion process after the A E A (−3 to −1) signal peptidase recognition site. It is notable that the region around the cysteine residue of this signal sequence shows close resemblance to a lipoprotein consensus signal peptide (see Von Heyne, ibid.).

The amino acid sequence predicted from the DNA sequence indicates that mature M-1 lipase consists of a 289 amino acid protein terminating with a TGA stop codon (see FIG. 12). The predicted molecular weight of this mature protein is 30,323 which is in close agreement with the molecular weight determined for the M-1 lipase (MW 31,500) by SDS-polyacrylamide gel-electrophoresis (see FIG. 10).

EXAMPLE 5

Molecular Cloning of the *Pseudomonas aeruginosa* PAO Lipase Gene

The lipase of *Pseudomonas aeruginosa* is a lipid-hydrolyzing enzyme (EC 3.1.1.3), having a MW of about 29,000, which is secreted into the medium during the late exponential growth phase (see Stuer et al., J. Bacteriol. 168 (1986) 1070–1074).

A. Cloning and Characterization

To clone the lipase gene from the *Pseudomonas aeruginosa* PAO 1 strain (ATCC 15692), a broad host range cloning system was used which enabled the gene bank to be screened directly by complementation against various mutant strains of Pseudomonaceae. The broad host range vector pKT248 (Bagdasarian et al., Gene 16 (1981) 237–247) was used, which is a mobilizable R300B-derived broad host range plasmid conferring streptomycin and chloramphenicol resistance.

*Pseudomonas aeroginosa* PAO 1 DNA was partially digested with restriction endonuclease SalI and ligated into the single SalI site of the pKT248 vector. The ratio of insert:vector was 5:1 to reduce the possibility of vector-to-vector ligation. The ligated PAO/pKT248 DNA was transformed into competent *E. coli* SK1108 (Donovan and Kushner, Gene 25 (1983) 39–48) as described in Example 1B. Transformants of *E. coli* SK1108 were selected for streptomycin resistance ($Sm^R$) and contraselected for chloramphenicol sensitivity ($Cm^S$).

Six-thousand (6,000) $Sm^RCm^S$ clones were obtained and screened for lipolytic activity as described in Example 2. None of the clones showed such activity, probably due to the poor recognition of Pseudomonas promoters in *E. coli* (Jeenes et al., supra).

Transfer of the clones from *E. coli* to *Pseudomonas aeruginosa* PAO 2302 lipase-negative mutant 6-1 (Wohlfarth and Winkler, J. Gen. Microbiol. 134 (1988) 433–440) was therefore performed as follows: 6,000 clones were divided into 120 portions each consisting of 50 clones. Plasmid preparations were obtained from each portion and used to transform competent cells of the PAO 2302 (6-1) lip-mutant. Competent Pseudomonas cells were prepared according to Olsen et al., J. Bacteriol. 150 (1982) 60–69. Selection was made on calciumtriolein (CT) agar plates (Wohlfarth and Winkler, supra), supplemented with streptomycin (50 $\mu$g/ml). Ten of the 5,000 screened PAO transformants showed lipase activity as evidenced by white crystals on top of the colonies. One of these positive PAO transformants, pSW1, was chosen for further characterization.

The plasmid contained therein was characterized by restriction analysis followed by electrophoresis on agarose gels and was found to contain a SalI insert of 3.1 kb composed of a 1.3 kb, a 0.97 kb and a 0.76 kb SalI subfragment. These inserts were subcloned in appropriate vectors for DNA sequencing and for obtaining expression of the lipase gene.

Plasmid DNA from a pUC19 derived subclone, named pSW103 (which contained the 1.3 and 0.97 kb inserts), was isolated and characterized with restriction endonucleases. The physical map of this plasmid pSW103 is presented in FIG. 13. A sample of *E. coli* JM101 hsdS recA harbouring plasmid pSW103 was deposited with CBS on Mar. 8, 1989 under No. 141.89.

B. Sequencing and Characterization of the *Pseudomonas aeruginosa* PAO 1 Lipase Gene The 2.3 kb SalI insert of pSW103 containing the PAO 1 lipase gene was sequenced by two procedures: both a "forced" cloning sequencing as well as a "shot-gun" cloning sequencing method of Deininger (Anal. Biochem. 129 (1983) 216–223) on the M13 bacteriophage derivatives mp18 and mp19 (Yanisch-Perron et al., Gene 33 (1985) 103–119) and the dideoxy chain termination technique according to Mizusawa et al., Nucleic Acids Res. 14 (1986) 1319–1324.

In the "forced" cloning sequencing procedure SalI/PstI and SalI/EcoRI fragments of the 2.3 kb insert of pSW103 were purified and ligated into an appropriate M13mp18 vector. The entire sequence was established by merging the collection of the obtained pieces of DNA sequence. Most of the DNA sequence has been determined for both strands. This DNA sequence when translated in all possible reading frames revealed that only the 0.97 kb SalI fragment of pSW103 (see FIG. 14) encodes for the mature PAO 1 lipase.

The 1.3 kb SalI fragment of the pSW103 subclone did not encode for, when translated in all possible reading frames, the 24 N-terminal amino acid residues of the PAO 1 lipase protein as determined by direct amino acid sequencing.

The amino acid sequence predicted from the DNA sequence of the 0.97 kb SalI fragment indicates one interesting domain (designated with A in FIG. 14).

Domain A encodes for an amino acid sequence G-H-S-H-G which was already defined as the active center of both eukaryotic lipases (Wion et al., Science 235 (1987) 1638–1641; Bodmer et al., Biochem. Biophys. Acta 909 (1987) 237–244) and prokaryotic lipases (Kugimiya et al., Biochem. Biophys. Res. Commun. 141 (1986) 185–190).

EXAMPLE 6

A. Expression of Cloned M-1 Lipase in Bacteria

To improve the expression level of the M-1 lipase in heterologous hosts the 2.0 kb KpnI-HindIII fragment of pTMPv18A carrying the M-1 lipase gene was ligated into KpnI and HindIII digested pBHA/C1 vectors. The nucleotide sequence of the pBHA1 vector is described in EP-A-0275598. The pBHC1 vector is identical to the PBHA1 vector except for the difference in expression of the following antibiotic resistance genes: the chloramphenicol-acetyltransferase gene (Cm) is expressed in *E. coli* strain WK6 harbouring the pBHC1 vector and the beta-lactamase gene (Ap) is expressed in *E. coli* strain WK6 harbouring the pBHA1 vector. The *E. coli* WK6 strain is described by R. Zell and H. J. Fritz, EMBO J. 6 (1987) 1809.

After transformation of WK6 and analysis of either the obtained ampicillin resistant colonies (in case of pBHA1) or the obtained chloramphenical resistant colonies (in case of PBHC1), the respective plasmids pBHAM-1 and pBHCM-1 were found, see FIG. 15.

The next step was the introduction of a NdeI restriction endonuclease site on the ATG initiation codon of the M-1 preprotein. Site-directed mutagenesis on the pBHA/CM-1 plasmids was performed as described by Stanssens et al., in "Protein Engineering and Site-Directed Mutagenesis", 24th Harder Conference (1985), Ed. A. R. Fersht and G. Winter.

After mutagenesis potential mutants were checked on having the relevant mutation by both restriction enzyme analysis and sequence analysis using the dideoxy method of Mizusawa et al., see Example 5. After these analyses, the correct plasmid, designated pBHAM1N1, was found (see FIG. 16). In order to achieve the regulated expression of the M-1 lipase in *E. coli* the 1.7 kb NdeI-HindIII fragment of pBHAM1N1 containing the M-1 lipase structural gene was isolated and ligated into two expression vectors;

pTZ18RN, a pTZ18R derivative which contains a unique NdeI site on the ATG initiation codon of beta-galactosidase (see Mead et al., Protein Engineering 1 (1986) 67–74);

pMCTN, a pMC derivative (see Stanssens et al., supra) containing a unique NdeI site behind a tac promoter and ribosomal binding site.

After transformation of the two ligations into competent *E. coli* JM-101 hsdS recA cells the obtained transformants were screened for lipolytic activity on tributyrin agar plates which contained 0.5 mM IPTG (isopropyl-β-D-thiogalactoside). After incubation of these tributyrin plates at 30° C. for 48 h followed by storage of the plates in the refrigerator during several days some colonies formed a weak halo, showing lipolytic activity. The plasmids of these tributyrin positive clones were characterized by restriction enzyme analysis. The two plasmids searched for were found:

pTZN1M1 which harbours the M-1 lipase gene behind the lac control sequences (see FIG. 17); and pMCTM1 which harbours the M-1 lipase gene behind the tac control sequences (see FIG. 18).

To identify the lipolytic activity produced by *E. coli* transformants harbouring the plasmids pTZN1M-1 and pMCTM-1, respectively, these clones were grown overnight in 100 mls 2 TY medium (16 g/l Bacto tryptone, 10 g/l Bacto-yeast extract, 5 g/l NaCl, pH 7.0) at 30° C. followed by a 3 h induction with 0.5 mM IPTG at 30° C. *E. coli* strain JM-101 hsdS recA harbouring pTZ18RN was used as a negative control. The cells were separated from the culture supernatant by centrifugation and then fractionated into periplasmic and membrane/cytoplasmic components according to Tetsuaki et al., Appl. Environmental Microbiol. 50 (1985) 298–303. Each fraction was analyzed on SDS-polyacrylamide gels according to Laemmli, Nature 227 (1970) 680–685 consisting of a 13% separation gel and a 5% stacking gel. The gels were run at 60 mA until the Bromophenol Blue (BPB) marker reached the bottom of the gel. Sample preparation and protein blotting procedure were performed as described in EP-A-0253455. The Western blot was analyzed by using polyvalent rabbit antisera against purified lipase from *P. pseudoalcaligenes* strain M-1. From the results shown in FIG. 19 it can be concluded that *E. coli* strains harbouring pTZN1M1 and pMCTM1, respectively, can synthesize and secrete into the periplasmic space a M-1 lipase specific 31.5 kDa polypeptide (see FIG. 19, lanes B and C). The lipolytic activity of this 31.5 kDa polypeptide was confirmed by the soft agar overlay technique based on the β-naphthyl acetate/Fast Blue BB salt method, described in Example 1C.

EP-A-0275598 and EP-A-0253455 disclose a method for efficient transfer to Bacillus of a vehicle containing a gene of interest, resulting in Bacillus strains which secrete effectively the desired polypeptide products. This method was used for both the Thai IV 17-1 and the M-1 lipase genes.

In case of the M-1 lipase gene the pBHAM1N1 plasmid (see above) was digested with NdeI and religated. The ligation mixture was transformed into *Bacillus licheniformis* T9 protoplasts. A number of neomycin resistant tributyrin positive colonies were analyzed and the correct plasmid was obtained. The plasmid was called pBHM1N1 (see FIG. 20) with the M-1 preprotein behind the HpaII promoter of pUB110 (see Zyprian and Matsubara, DNA 5 (1986) 219–225). T9 transformants harbouring the pBHM1N1 plasmid were tested for their ability to hydrolyze β-naphthyl esters after fermentation in industrial broth according to the method described in Example 2. The results indicate that the lipolytic activity of the enzyme produced by the T9 clones have similar characteristics to that of the lipase obtained from the parent *Pseudomonas pseudoalcaligenes* M-1 strain.

For expression in Pseudomonas hosts the constitutive promoter of the p78 gene from the Pseudomonas specific bacteriophage Pf3 was used (see R. G. M. Luiten, "The Filamentous Bacteriophage Pf3: A Molecular Genetic Study", PhD Thesis 1987, Catholic University of Nijmegen, The Netherlands). A synthetic DNA fragment was made encoding this Pf3 promoter:

This fragment was ligated into vector pTZ18R cleaved with EcoRI and KpnI giving rise to plasmid pTZPf31A. The plasmids pTZPf31A and pMCTM1 were cleaved both with BamH1 and HindIII, ligated and transformed to competent *E. coli* JM-101 hsdS recA cells. The correct plasmid in which the M-1 lipase gene is placed under the control of the Pf3 promoter was obtained and called pTZPf3M1.

In order to achieve expression of the cloned M-1 lipase gene in pseudomonads the M-1 expression cassettes present in the plasmids pTMPv18A, pMCTM1 and pTZPf3M1 were inserted into the broad host range vectors pKT231 (Bagdasarion et al., Gene 16 (1981) 237–247), pLAFR3 (Staskawisz et al., J. Bacteriol. 169 (1987( 5789–5794) and pJRD215 (Davison et al., Gene 51 (1987) 275–280). The obtained broad host range plasmids harbouring the M-1 expression cassettes were transferred according to the triparental mating procedure of Friedman et al., Gene 18 (1982) 289–296) to the following Pseudomonas strains:

the lipase negative mutant 6-1 of P. aeruginosa strain PAO 2302 (Wohlfarth and Winkler, supra).

the lipase negative P. putida strain KT2442 (Zeyer et al., Applied Environmental Microbiol. 50 (1985) 1409–1413)

the P. pseudoalcaligenes strain M-1 (CBS 473.85)

the P. pseudoalcaligenes strain IN II-5 (CBS 468.85)

As an alternative procedure for the transfer of the broad host range plasmids from E. coli to Pseudomonas the electric field-mediated transformation ("electroporation") procedure was used according to the manual of Gene Pulser (Bio-rod Laboratories).

The obtained Pseudomonas transformants were tested for their lipase production after fermentation in olive oil based media as described by Odera et al, J. Ferment. Technol. 64 (1986) 363–371.

In the following Table 2 the lipolytic productivity of the various strains is shown.

TABLE 2

Lipase Productivity of Certain Transformed Pseudomonas Strains Containing the M-1 Lipase Gene

| Pseudomonas strain | Broad host range vector harbouring the M-1 expression cassette from | Lipase productivity in %* |
| --- | --- | --- |
| PAO2302(6-1) | no insert (vector) | 0 |
| PAO2302(6-1) | pTMPv18A | 2 |
| PAO2302(6-1) | pMCTM1 | 40 |
| PAO2302(6-1) | pTZPf3M1 | 60 |
| KT2442 | no insert (vector) | 0 |
| KT2442 | pTMPv18A | 1 |
| KT2442 | pMCTM1 | 30 |
| KT2442 | pTZPf3M1 | 40 |
| M-1 | no insert (vector) | 100 |
| M-1 | pTMPv18A | 340 |
| M-1 | pMCTM1 | 240 |
| M-1 | pTZPf3M1 | 260 |
| IN II-5 | no insert (vector) | 100 |
| IN II-5 | pTMPv18A | 420 |
| IN II-5 | pMCTM1 | 350 |
| IN II-5 | pTZPf3M1 | 270 |

*The lipolytic productivity was determined on culture supernatants using the method described in Example 2.

The lipases produced by these Pseudomonas transformants were analyzed by SDS gel-electrophoresis and migrated identically to the lipase produced from the original P. pseudoalcaligenes strain M-1.

It can be seen that the improvement achieved by the introduction of multiple copies of the M-1 expression cassettes in P. pseudoalcaligenes strains is 2–4 fold compared with the level of lipase produced by the donor strain. Moreover, it can be concluded that the original gene expression initiation signal or promoter of the M-1 lipase gene is active in Pseudomonas pseudoalcaligenes strains, in contrast to the PAO 1 and KT2442 strains.

B. In Vitro Expression of the Cloned M-1 Lipase Gene

In vitro expression of the M-1 lipase containing clones was performed using a prokaryotic DNA-directed translation kit (Amersham International). This system allows the in vitro expression of genes contained on a bacterial plasmid provided that the relevant control signals are present. The following four bacterial plasmids were analyzed:

B.1. Plasmid pTMPv18A (see FIG. 11) encoding both M-1 lipase and β-lactamase gene products, supplying ampicillin (Ap) resistance. Furthermore, pTMPv18A carries its own regulation signals, promoter, Shine-Dalgarno and leader sequence.

B.2. Plasmid pMCTM1 (see FIG. 18) carrying the M-1 lipase gene and the chloroamphenicol resistance gene (Cm). In this construct the lipase promoter is exchanged by a strong tac promoter.

B.3. Plasmid pMCTbliM1 carries also the M-1 lipase gene and the chloroamphenicol resistance gene. In this construct the lipase signal sequence was exchanged by the α-amylase signal sequence (see EP-A-0224294). The promoter was the same as in construct pMCTM1.

B.4. Plasmid pTZ18RN (see FIG. 17) was used as a negative control.

DNA (0.5 μg) of the mentioned plasmids was transcribed in vitro. This reaction was carried out by adding 0.5 μl of 10×TB/10×NTP mix (a mixture of equal volumes of 20×TB and 20×NTP mix; 20×TB contains 800 mM Tris HCl pH 7.5, 120 mM $MgCl_2$ and 40 mM spermidine; 20×NTP mix contains 10 mM ATP, 10 mM CTP, 10 mM GTP and 10 mM UTP), 0.5 μl of 0.1M DTT, 0.5 μl of RNasin (40 u/μl, Promega) and 0.5 μl of T7 RNA polymerase (15 u/μl, Promega) or 1 μl of E. coli RNA polymerase (1 u/μl, Boehringer). The reaction mixture was incubated for 1 h at 39.5° C.

In vitro translation of the RNA transcripts was performed according to the instructions supplied by the manufacturer. M-1 lipase was immunoprecipitated as described by Van Mourik (J. Biol. Chem. 260 (1985) 11300–11306) using monoclonal antibodies against M-1 lipase.

As a negative control pTZ18RN was used (FIG. 21, lanes A and E). Immunoprecipitation of pTMPv18A (lane B) reveals an unprocessed M-1 lipase of 34 kDa. Immunoprecipitation of pMCTM-1 (lane C) reveals an unprocessed M-1 lipase of 34 kDa and the mature M-1 lipase of 31.5 kDa, whereas immunoprecipitation of pMCTbliM1 (lane D) reveals the mature M-1 lipase of 31.5 kDa. From the in vitro translation experiments it can be concluded that the M-1 lipase gene can be expressed in S-30 extracts of E. coli cells. The data obtained by in vitro transcription/translation of pTMPv18A support the absence of lipolytic activity on tributyrine plates (see Example 4B) for there is no processing of M-1 lipase.

EXAMPLE 7

Molecular Enzyme Screening Using Characterised Lipase Genes as Probes

To further demonstrate the general applicability of the invention we used the probes disclosed in this application to search for lipase genes with comparable characteristics, originated from other micro-organisms. We demonstrate that we are able to select lipase genes encoding lipases which have the same or comparable washing applicability.

As an example we describe the use of DNA inserts of plasmids pET3 and pTMPv18A, respectively, as hybridization probes to show that homologous genes of both are present in most of the analyzed micro-organisms. There is no cross-hybridization between the two lipase genes (lane A and lane B) suggesting that each of these lipase encoding sequences originate from different ancestor genes.

In Example 8, we also demonstrate that this hybridization technique enables us to clone homologous lipase genes from other microorganisms.

In order to achieve this, chromosomal DNA from the following strains, *Pseudomonas pseudoalcaligenes* M-1 (CBS 473.85), *P. pseudoalcaligenes* IN II-5 (CBS 468.85), *P. alcaligenes* (DSM 50342) *P. aeruginosa* (PAC 1R (CBS 136.85), *P. aeruginosa* PAO (ATCC 15692) (Wohlfarth and Winkler, 1988, J. Gen. Microbiol. 134, 433–440). *P. stutzeri* Thai IV 17-1 (CBS 461.85); *P. stutzeri* PG-I-3 (CBS 137.89), *P. stutzeri* PG-I-4 (CBS 138.89), *P. stutzeri* PG-II-11.1 (CBS 139.89), *P. stutzeri* PG-II-11.2 (CBS 140.89), *P. fragi* DB1051, *P. gladioli* (CBS 176.86), *Acinetobacter calcoaceticus* Gr-V-39 (CBS 460.85) and *Staphylococcus aureus* (ATCC 27661) was isolated, 5 µg was digested and analyzed by the Southern blotting technique (Maniatis et al., supra). DNA was transferred to a nitrocellulose filter (Schleicher & Schuell, BA85; 0.45 mM). Filters were pre-hybridized in 6×SSC, 5×Denhardt, 0.5% SDS and 100 µg/ml of denatured calf thymus DNA.

After two hours of pre-incubation 32P labeled insert of respectively pTMPv18A or pET3 was added and hybridization was carried out at 55° C. during 16 hours.

Insert DNAs were isolated by digestion of pTMPv18A with XhoI and EcoRV and digestion of pET3 with EcoRI, followed by separation of the fragments by 0.8% agarose gel electrophoresis and recovering of the fragments by the glass milk procedure (Gene Clean™). The insert of pTMPv18A, a 1 kb XhoI/EcoRV fragment and the insert of pET3, a 3.2 kb EcoRI fragment were labeled in vitro to high, specific activity (2–5 $10^8$ cpm/µg) with α32P ATP by nick translation (Feinberg and Vogelstein, Anal. Biochem. 132, 1983, 6–13). It was shown that probe fragments have an average length varying from 300–800 bases.

Filters were then washed twice for 30' at 55° C. in 6×SSC, 0.1% SDS. Filters were dried at room temperature and autoradiographed for 1–3 days by exposure to KODAK X-omat AR films or Cronex 4 NIF 100 X-ray film (Dupont) with intensifying screens at −70° C. (Cronex lightning plus GH 220020).

The following equation, which has been derived from analysing the influence of different factors on hybrid stability:

$$Tm=81+16,6(\log 10\ Ci)+0.4(\%\ G+C)-600/n-1.5\%$$

mismatch (Current protocols in molecular biology 1987–1988, edited by Ausubel et al.)
n=length of the shortest chain of the probe
Ci=ionic strength (M)
G+C=base composition
was used to determine the homology which could be detected in our experiments. Assuming a probe length of 300 bases, we were able to detect a homologous gene which shows at least 67% homology within a fragment of 300 bases or more. In the determination of homology percentage we assumed that the GC contents of Pseudomonas is 65% (Normore, 1973, in Laskin and Lechevalier (ed), Handbook of microbiology vol II, CRC press, Inc. Boca Raton. Fla.)

FIG. 22A shows the hybridization pattern of the SalI digested chromosomal DNAS, when hybridized with the EcoRI insert of pET3. It can be seen that most of the Pseudomonas strains, contain homologous genes to our pET3 clone. In *P. fragi* DB 1051 (lane M), *A. calcoaceticus* Gr-V-39 (lane O ) and *S. aureus* (lane P) no homologous genes were detected. Moderate hybridization signals were observed in *P. alcaligenes* (lane E), *P. pseudoalcaligenes* (lane C and lane D), *P. aeruginosa* (lane F and lane G) whereas weak hybridization was observed in *P. gladioli* (lane N). Very strong hybridization was seen in *P. stutzeri* strains (lane H to L), which is not surprising since pET3 was originally derived from *P. stutzeri* ThaiIV 17-1.

FIG. 22B shows the hybridization pattern with the EcoRV/XhoI insert of pTMPv18A.

It can be seen that strong hybridization signals were obtained from chromosomal DNAs of *P. pseudoalcaligenes*, (lane C and D), *P. alcaligenes* (lane E) and *P. stutzeri* strains (lane H to lane L). Weaker hybridization was seen in chromosomal DNAs of *P. aeruginosa* (lane F and G) and no hybridization at all was found with chromosomal DNAs of *P. fragi* DB1051 (lane M), *P. gladioli* (lane N), *A. calcoaceticus* Gr-V-39 (lane O) and *S. aureus* (lane P).

EXAMPLE 8

Cloning of Homologous Lipase Genes From Other Microorganisms

In order to demonstrate the applicability of the invention disclosed, we describe the use of plasmid PTMPv18A to clone a homologous gene originated from *P. alcaligenes* (DSM 50342) (see FIG. 22B, lane E).

In FIG. 22B, lane E, it can be seen that *P. alcaligenes* shows a clear 5.0 kb SalI fragment and a faint 0.5 kb SalI fragment, which hybridize with the probe. This indicates that *P. alcaligenes* contains a gene which has at least 67% homology within a fragment of 300 basepairs or more to the XhoI/EcoRV insert of the pTMPv18A plasmid.

To establish whether the 5.0 kb SalI fragment of *P. alcaligenes* represents a gene encoding a lipase SalI fragments were cloned. A SalI gene library was constructed with the aid of vector pUC19 and transformed into *E. coli* JM109 (Yanish-Perron et al., Gene 33 (1985) 103–119). Replica filters of the gene library were hybridized with the α32P-labeled insert of pTMPv18A using conditions as described in Example 7. Three positive clones, which all carried a 5.0 kb SalI fragment, were isolated from the library: pCH1, pCH2 and pCH3. the 5.0 kb SalI fragment of pCH1 was recloned into vector pKT248 (Bagdasarian et al., Gene 16 (1981) 237–247) with the aid of the SalI site, which is located in the chloramphenicol-resistance gene. Streptomycin-resistant chloramphenicol-sensitive transformants were selected in *E. coli* JM109. One of these transformants, pCH101, which contained the expected 5.0 kb SalI insert was transformed into *Pseudomonas aeruginosa* 2302 (6-1) lip- (see Example 5).

Colonies were grown on NB-calcium triolein agar. After growth, plates were stored at 10° C. After several days a calcium precipitate was visible around the transformed colonies and not around non-transformed *P. aeruginosa* 2302 (6-1) lip-, which was grown on similar agar plates without antibiotics. We conclude that the cloned 5.0 kb SalI fragment complements the lip- phenotype of *P. aeruginosa* 2302 (6-1) lip- and therefore encodes an extracellular lipase, which can be produced in a suitable host.

On the basis of the DNA hybridization experiments it can be concluded that this lipase shows homology to M-1 lipase and consequently to the other lipases, hybridizing with the pTMPv18A insert, used as a probe. The description of the cloning of *P. alcaligenes* lipase represents a generally applicable method to clone lipase genes that show homology to M-1 lipase.

EXAMPLE 9

Comparison of the Nucleotide Sequence of the Lipase Obtained From *Pseudomonas pseudoalcaligenes* M-1 With Other Lipases The nucleotide sequence of *Pseudomonas pseudoalcaligenes* M-1 lipase (FIG. 12) was compared to that of

*Pseudomonas fragi* (IFO-3458) lipase (Kugimiya et al., Biochem. Biophys. Res. Commun. 141 (1986) 185–190), *Staphylococcus hyicus* lipase (Gotz et al., Nucleic Acids Res. 13, (1985) 1891–1903) and *Pseudomonas aeruginosa* PAO1 lipase (FIG. 14). A close homology of 81% was found between M-1 lipase and *P. aeruginosa* PAO1 lipase and a homology of 62% was found between M-1 lipase and *P. fragi* (IFO-3458). However, the sequence of this *P. fragi* lipase is remarkably shorter than the sequence of the two other Pseudomonas lipases. No homology was found between M-1 lipase and *Staphylococcus hyicus* lipase.

These results support the data obtained in Example 7, where no hybridization was detected with (chromosomal DNA) derived from *Pseudomonas fragi* and *Staphylococcus aureus*, when pTMPv18A was used as a probe.

The amino acid sequence derived from the nucleotide sequence of *P. pseudoalcaligenes* M-1 lipase was also compared to other lipases. Overall homology between M-1 lipase and *P. aeruginosa* PAO1 lipase was found to be (78%) and between M-1 lipase and *P. fragi* lipase to be 48%. Again no homology was found between the amino acid sequence of M-1 lipase and *Staphylococcus hyicus* lipase. However, close homology does exist between the four lipases in the region of the essential serine 87 of mature M-1 lipase. Kugimiya et al., (supra), postulated that the sequence of this region G-H-S-H-G is the active center of lipase enzymes.

EXAMPLE 10

Detergent Compatibility of Homologous Lipases in the SLM-Test

This example illustrates the performance of the lipase enzymes produced by *P. aerugiuosa, P. stutzeri* and *P. alcaligenes* strains which show a high degree of DNA sequence homology with the M-1 gene, in a washing process according to the modified SLM-test where the compatibility of these enzymes in modern laundry cleaning composition was tested.

The cleaning compositions used were a powder detergent composition (ALL®-base, described in EP-A-0218272) and a liquid detergent formulation (Liquid TIDE®, also described in EP-A-0218272, but without inactivation of the protease). The lipase enzymes were prepared by culturing the bacteria according to the following procedure: an inoculum culture was prepared by culturing the bacteria in 100 ml Brain Heart Infusion (BHI) medium in a rotary shaker at 30° C., for 24 hours. A lab-fermentor (2 liters) containing 1.0 liter of a medium with the composition mentioned below was then inoculated.

| Composition of the medium | |
|---|---|
| Component | Concentration (g/kg) |
| Brain Heart Infusion (BHI) (Difco) | 18.50 |
| Yeast Extract (Difco) | 16.00 |
| Calcium Chloride.2H$_2$O | 0.80 |
| Magnesium Sulfate.7H$_2$O | 3.20 |
| Manganese Sulfate.1H$_2$O | 0.030 |
| Soya Oil | 5.0 |
| Dipotassium Phosphate | 6.40 |

The fermentation was run at 30° C. Sixteen hours after inoculation a feed of soya oil was started at the rate of 1 g/h and continued for the rest of the fermentation. The aeration rate was 60 l/h and the agitation rate 700 rpm. The fermentation was run for a total of 64 hours.

After the fermentation the bacteria were removed by centrifugation. The supernatant was mixed rapidly under stirring with 2.5 volumes of acetone at room temperature. The mixture was then stirred for 10 minutes, allowed to settle and filtered through a glass filter, under suction. The filter cake was then washed with 70% acetone followed by 100% acetone and then dried under vacuum.

The lipase enzyme preparations obtained in this way were then tested in the SLM-test procedure. The procedure for the SLM test has been described in EP-A-0218272. This procedure was modified as follows:

A volume of 20 μl containing 10 mg olive oil dissolved in acetone (25%) was spotted on a polyester Swatch (3×3 cm), and air dried at room temperature. A washing solution consisting of 10 ml of SHW (Standard Hardness Water: 0.75 mM CaCl$_2$, 0.25 mM MgCl$_2$) or detergent dissolved in SHW was placed in an Erlenmeyer flask (25 ml) with a ground stopper and kept in a shaking water-bath at 40° C. The detergents tested were a powder detergent composition (ALL® base) and a liquid formulation (TIDE® liquid). The concentration of ALL base washing solution was 4 g/l (pH 9.5). The concentration of liquid TIDE was 1.5 g/l (pH 7.5). The solutions were buffered with 0.1M Tris/HCl. The washing process was started by adding the enzyme preparation and immediately thereafter the soiled swatch, to the Erlenmeyer flask and shaking for 40 min or longer at 40° C. The final lipase concentration was 2 TLU/ml.

After washing, the swatch was rinsed with SHW then dried at 55° C. for one hour. The dried swatches as such were washed again in a second wash cycle using a fresh detergent and enzyme solution for 40 minutes. After the second cycle wash the swatch was treated with 0.01N HCl for 5 min, rinsed and dried at room temperature overnight. The dried swatches were extracted by rotation in a glass tube containing a 5 ml of solvent (n-hexane/isopropylalcohol/formic acid: 975:25:2.5 (v/v), 1 ml/min). The residual triglyceride, diglyceride and the free fatty acid formed were determined by HPLC.

HPLC Equipment and Conditions:
Column: CP Microspher-Si (Chrompack), 100×4.6 mm
Injection system: Wisp (Millipore) 10 μl
Pump: Model 2150 (LKB)
Detection: Refractive index monitor (Jobin Jvon)
Integrator: SP 4270 (Spectra Physis)
Eluent: n-hexane/isopropylalcohol/formic acid: 975:25:2.5 (v/v), 1 ml/min.
Temperature: ambient The retention time of triolein was 1.2 min., that of 1,3 diglycerides was 2.5 min., that of 1,2 diglycerides was 3.6 min. and that of oleic acid was 1.6 min. The peak area or peak height was determined as an indication of the recovery of the triglyceride and fatty acid. The recovery of triglyceride after extraction from the unwashed swatch was taken as 100%. The ratio of the refractive index responses between triolein and oleic acid was found to be 1.0 on the basis of peak height.

The results of these SLM-tests are shown in the following tables. In these tables the triglycerides recovery and the total lipids recovery are shown. Total lipids recovery is triglycerides plus 1,2- and 1,3-diglycerides plus free fatty acids. The difference between total lipids recovery and triglycerides recovery is a measure of lipase activity and performance. The difference between the total lipid recovery and the control (without lipase enzyme) indicates the removal of oily stain from the fabric and demonstrates that these enzymes are stable and effective under realistic washing conditions, as simulated in the SLM-test.

TABLE 3

SLM testing results of various lipases in Liquid Tide ® composition

| Isolate | Strain | Activity of Preparation (TLU/g) | Tri-glycerides Recovery (%) | Total Lipids Recovery (%) |
|---|---|---|---|---|
| (Control) | — | 0 | 94.3 | 95.4 |
| P. pseudoalcaligenes | M-1 | 70580 | 9.0 | 44.2 |
| " | In II-5 | 12290 | 15.6 | 45.1 |
| P. aeruginosa | PAC 1R | 3310 | 27.1 | 59.8 |
| P. stutzeri | PG-I-3 | 6940 | 23.5 | 51.7 |
| " | PG-I-4 | 62270 | 70.5 | 81.1 |
| " | PG-II-11.1 | 28670 | 58.7 | 75.3 |
| " | PG-II-11.2 | 30910 | 70.8 | 82.5 |

TABLE 4

SLM-testing results of various lipases in ALL ®-base composition

| Isolate | Strain | Activity of Preparation (TLU/g) | Tri-glycerides Recovery (%) | Total Lipids Recovery (%) |
|---|---|---|---|---|
| (Control) | — | 0 | 95.0 | 95.3 |
| P. pseudoalcaligenes | M-1 | 70580 | 86.6 | 91.7 |
| " | In II-5 | 25000 | 78.9 | 86.2 |
| P. aeruginosa | PAC 1R | 3310 | 40.2 | 49.3 |
| P. stutzeri | PG-I-3 | 6940 | 61.4 | 71.8 |
| " | PG-I-4 | 62270 | 77.8 | 85.3 |
| " | PG-II-11.1 | 28670 | 78.4 | 86.7 |
| " | PG-II-11.2 | 30910 | 78.3 | 85.6 |

We claim:

1. A method for using a transformed Pseudomonas host cell for producing a lipolytic enzyme, said method comprising:

cultivating in a nutrient medium, a plurality of transformed Pseudomonas host cells for a sufficient time for said cells to express a recoverable quantity of said lipolytic enzyme, wherein said cells comprise an expression cassette which comprises as components in the 5'–3' direction of transcription, wherein said components comprise (1) a transcriptional regulatory region and a translational initiation region; (2) a DNA sequence obtained from Pseudomonas pseudoalcaligenes and encoding a lipolytic enzyme, wherein said enzyme is characterized as (a) being encoded by DNA with a high degree of hybridization to that DNA sequence shown in FIG. 12, (b) a pH optimum in the range of 8 to 10.5, measured in a pH-stat under conditions of TLU determination, and (c) exhibiting lipase activity in an aqueous solution containing a detergent at a concentration up to 10 g/l of solution under washing conditions at a temperature of 60° C. or below and at a pH between 7 and 11; and (3) translation and transcriptional termination regions, wherein said components are operably joined and functional in said host cell and expression of said DNA sequence is regulated by said transcriptional and translational regions; and recovering said lipolytic enzyme.

2. The method according to claim 1, wherein said expression cassette further comprises a marker gene.

3. The method according to claim 1, wherein a nucleotide sequence encoding a leader sequence is joined in proper reading frame to the 5' end of said DNA sequence.

4. The method according to claim 1, wherein said DNA sequence is obtained from Pseudomonas pseudoalcaligenes M-1 (CBS 473.85).

5. A method for preparing a lipolytic enzyme, said method comprising:

growing in a nutrient medium a plurality of transformed Pseudomonas host cells comprising a DNA sequence obtained from Pseudomonas pseudoalcaligenes, said DNA sequence characterized as having a high degree of hybridization to that DNA sequence shown in FIG. 12, and encoding a lipolytic enzyme which is characterized as (a) having a pH optimum in the range of 8 to 10.5, measured in a pH-stat under conditions of TLU determination, and (b) exhibiting lipase activity in an aqueous solution containing a detergent at a concentration up to 10 g/l of solution under washing conditions at a temperature of 60° C. or below and at a pH between 7 and 11, for a sufficient time for said cells to express a recoverable quantity of said lipolytic enzyme; and recovering said lipolytic enzyme.

6. A method of using a transformed Pseudomonas host cell to prepare a lipolytic enzyme, wherein said transformed Pseudomonas host cell comprises a DNA sequence obtained from Pseudomonas pseudoalcaligenes, said DNA sequence characterized as having a high degree of hybridization to that DNA sequence shown in FIG. 12, and encoding a lipolytic enzyme characterized as having (a) a pH optimum in the range of 8 to 10.5, measured in a pH-stat under conditions of TLU determination, and (b) exhibiting lipase activity in an aqueous solution containing a detergent at a concentration up to 10 g/l of solution under washing conditions at a temperature of 60° C. or below and at a pH between 7 and 11, said method comprising:

growing a plurality of said transformed Pseudomonas host cells in a nutrient medium for a sufficient time for said cells to express a recoverable amount of said lipolytic enzyme; and recovering said lipolytic enzyme.

7. The method according to claim 6, wherein said recovering is from said nutrient medium.

* * * * *